US012226203B2

(12) United States Patent
Ostadabbas et al.

(10) Patent No.: US 12,226,203 B2
(45) Date of Patent: Feb. 18, 2025

(54) METHOD AND SYSTEM FOR IN-BED CONTACT PRESSURE ESTIMATION VIA CONTACTLESS IMAGING

(71) Applicant: Northeastern University, Boston, MA (US)

(72) Inventors: Sarah Ostadabbas, Watertown, MA (US); Shuangjun Liu, Boston, MA (US)

(73) Assignee: Northeastern University, Boston, MA (US)

( * ) Notice: Subject to any disclaimer, the term of this patent is extended or adjusted under 35 U.S.C. 154(b) by 118 days.

(21) Appl. No.: 17/831,993

(22) Filed: Jun. 3, 2022

(65) Prior Publication Data

US 2022/0386898 A1    Dec. 8, 2022

Related U.S. Application Data

(60) Provisional application No. 63/196,268, filed on Jun. 3, 2021.

(51) Int. Cl.
*A61B 5/11* (2006.01)
*G06T 7/73* (2017.01)
(Continued)

(52) U.S. Cl.
CPC .......... *A61B 5/1116* (2013.01); *A61B 5/1128* (2013.01); *G06T 7/75* (2017.01);
(Continued)

(58) Field of Classification Search
CPC ... A61B 5/1116; A61B 5/1128; A61B 5/0035; A61B 2576/00; A61B 5/447; G06T 7/75; G06T 7/90; G06T 2207/10024; G06T 2207/10028; G06T 2207/10048; G06T 2207/20081; G06T 2207/30196; G06T 7/0012; G06T 2207/10016;
(Continued)

(56) References Cited

FOREIGN PATENT DOCUMENTS

CN    105877713 A  *  8/2016  .......... A47C 27/084

OTHER PUBLICATIONS

Liu et al 2019 arXiv:1907.02161v3 9pages (Year: 2019).*
(Continued)

*Primary Examiner* — Keith M Raymond
*Assistant Examiner* — Patrick M Mehl
(74) *Attorney, Agent, or Firm* — Verrill Dana, LLP

(57)    ABSTRACT

Provided herein are systems and methods for estimating contact pressure of a human lying on a surface including one or more imaging devices having imaging sensors oriented toward the surface, a processor and memory, including a trained model for estimating human contact pressure trained with a dataset including a plurality of human lying poses including images generated from at least one of a plurality of imaging modalities including at least one of a red-green-blue modality, a long wavelength infrared modality, a depth modality, or a pressure map modality, wherein the processor can receive one or more images from the imaging devices of the human lying on the surface and a source of one or more physical parameters of the human to determine a pressure map of the human based on the one or more images and the one or more physical parameters.

20 Claims, 19 Drawing Sheets

(51) Int. Cl.
*G06T 7/90* (2017.01)
*G06V 40/10* (2022.01)
*H04N 5/33* (2023.01)

(52) U.S. Cl.
CPC .............. *G06T 7/90* (2017.01); *G06V 40/10* (2022.01); *H04N 5/33* (2013.01); *G06T 2207/10024* (2013.01); *G06T 2207/10028* (2013.01); *G06T 2207/10048* (2013.01); *G06T 2207/20081* (2013.01); *G06T 2207/30196* (2013.01)

(58) Field of Classification Search
CPC ........... G06T 2207/20076; G06T 2207/20084; G06V 40/10; G06V 10/766; G06V 10/774; G06V 10/803; G06V 20/52; G06V 40/103; G06V 10/82; G06V 10/454; H04N 5/33
See application file for complete search history.

(56) References Cited

OTHER PUBLICATIONS

Palmero et al. 2017 Int. J. Comput. Vis. 122:212â227 (Year: 2016).*
Andriluka et al., 2014. 2d human pose estimation: New benchmark and state of the art analysis. In Proceedings of the IEEE Conference on computer Vision and Pattern Recognition, 3686-3693.
Cao et al., 2018. OpenPose: realtime multi-person 2D pose estimation using Part Affinity Fields. In arXiv preprint arXiv:1812.08008.
Clever et al., 2018. 3d human pose estimation on a configurable bed from a pressure image. In 2018 IEEE/RSJ International Conference on Intelligent Robots and Systems (IROS), 54-61. IEEE.
Liu et al., 2019. In-bed pose estimation: Deep learning with shallow dataset. IEEE journal of translational engineering in health and medicine 7: 1-12.
Martinez et al., 2015. Action recognition in bed using BAMs for assisted living and elderly care. In 2015 14th IAPR International Conference on Machine Vision Applications (MVA), 329-332. IEEE.
Murthy et al., 2009. Thermal infrared imaging: a novel method to monitor airflow during polysomnography. Sleep 32 (11): 1521-1527.
Newell et al., 2016. Stacked hourglass networks for human pose estimation. European Conference on Computer Vision 483-499.
Ostadabbas et al., 2015. A vision-based respiration monitoring system for passive airway resistance estimation. IEEE Transactions on biomedical engineering 63(9): 1904-1913.
Ostadabbas et al., 2011. Pressure ulcer prevention: An efficient turning schedule for bed-bound patients. Life Science Systems and Applications Workshop (LiSSA), 2011 IEEE/NIH 159-162.
Pham et al., 2015. Towards force sensing from vision: Observing hand-object interactions to infer manipulation forces. In Proceedings of the IEEE conference on computer vision and pattern recognition, 2810-2819.
Poh et al., 2010. Advancements in noncontact, multiparameter physiological measure ments using a webcam. IEEE transactions on biomedical engineering 58(1): 7-11.
Sun, K.; Xiao, B.; Liu, D.; and Wang, J. 2019. Deep High-Resolution Representation Learning for Human Pose Estimation. In CVPR, 12 pages.
Velardo et al., In 2010 Fourth IEEE International Conference on Biometrics: Theory, Applications and Systems (BTAS), 1-6. IEEE.
Wei et al., 2016. Convolutional pose machines. Proceedings of the IEEE Conference on Computer Vision and Pattern Recognition 4724-4732.
Yin et al., 2018. Geonet: Unsupervised learning of dense depth, optical flow and camera pose. In Proceedings of the IEEE Conference on Computer Vision and Pattern Recognition, 1983-1992.

* cited by examiner

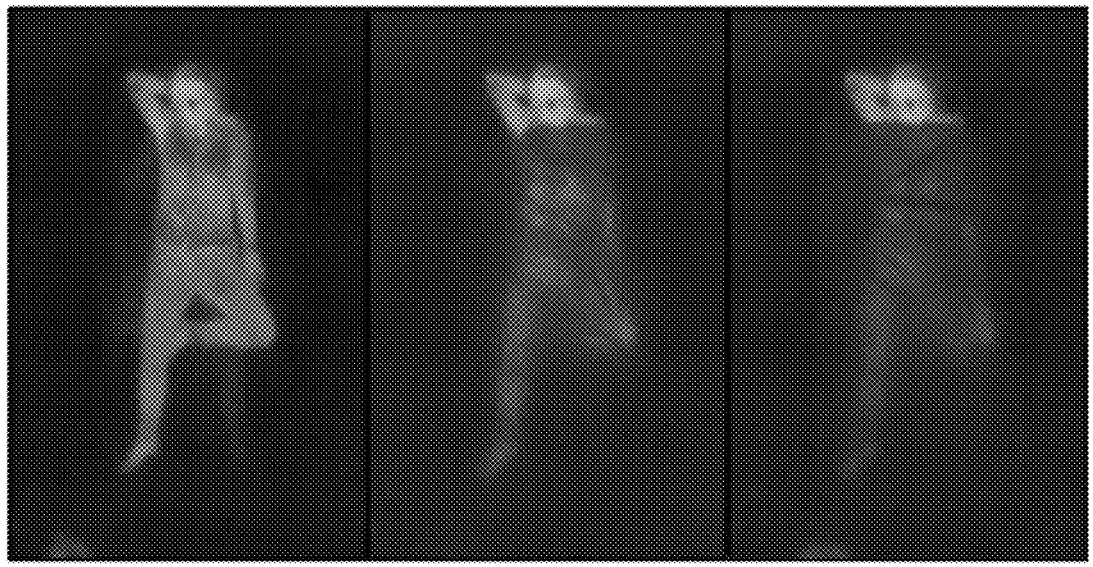
*FIG. 11G*  *FIG. 11H*  *FIG. 11I*
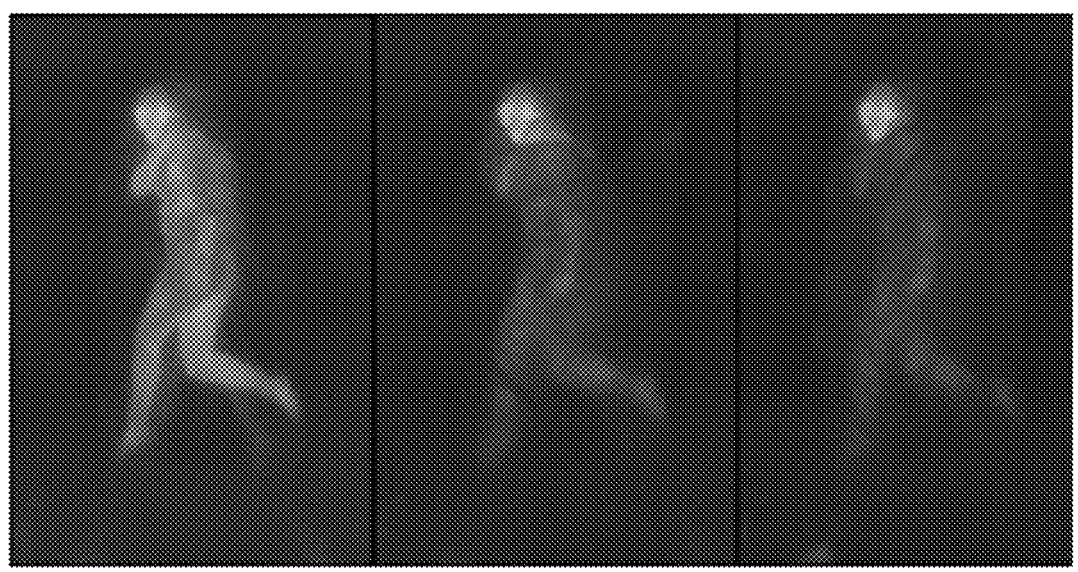
*FIG. 11J*  *FIG. 11K*  *FIG. 11L*

FIG. 13

METHOD AND SYSTEM FOR IN-BED CONTACT PRESSURE ESTIMATION VIA CONTACTLESS IMAGING

CROSS REFERENCE TO RELATED APPLICATIONS

This application claims benefit under 35 U.S.C. § 119(e) of U.S. Provisional Application No. 63/196,268, filed on 3 Jun. 2021, entitled "Method and System for In-Bed Contact Pressure Estimation Via Contactless Imaging," the disclosure of which is incorporated by reference herein.

STATEMENT REGARDING FEDERALLY SPONSORED RESEARCH OR DEVELOPMENT

This invention was made with government support under Grant Number 1755695 awarded by the National Science Foundation. The government has certain rights in the invention.

BACKGROUND

In the past few years, advances in the field of computer vision have been actively introduced into in-bed (or at-rest) behavior studies, including works related to sleep pose estimation, see Clever et al. 2018; Liu, Yin, and Ostadabbas (2019) or action recognition, see Martinez, Rybok, and Stiefelhagen (2015). One area that significantly benefits from automatic in-bed behavior monitoring is pressure ulcer (also known as bedsore) prevention and early detection studies in bed-bound patients. Pressure ulcers are localized injuries to the skin and/or underlying tissues usually over a bony prominence as a result of prolonged contact pressure caused by the bed surface. See Black et al. (2007). Pressure ulcers are extremely costly to treat and may lead to several other health problems, including death.

While regular repositioning (i.e. every two hours) of the bed-bound patients can help in the prevention of the pressure ulcers, patient repositioning often needs up to four caregivers at the same time to ensure the safety of the patient. This leads to a huge burden on our already overworked nursing staff. Knowing a patient in a particular body part experiencing high pressure can allow patient-specific care and an efficient workload management. See Ostadabbas et al. (2011).

Currently, the in-bed contact pressure monitoring systems mainly rely on the use of commercially available pressure mats, which are expensive and hard to maintain. See Ostadabbas et al. (2011).

Within less than a decade, computer vision has enabled machines to visually perceive physical or semantic properties of images/videos, including understanding scene contents, see Deng et al. (2009), segmenting them into distinct regions, see Chen et al. (2018), and tracking the objects and their poses, see Wei et al. (2016). Perceiving non-visual physical properties of an object in an image is also a subject recently explored by the computer vision community, such as finding total manipulation force due to hand-object interactions. See Pham et al. (2015), inferring force distribution along elastic objects, see Greminger and Nelson (2004), and estimating body weights, see Velardo and Dugelay (2010). The majority of this work focuses on estimating bulk physical properties such as weight or total force, rather than on providing a dense map of the physical quantity of interest. Visual signals are often employed for displacement measurement purposes, while problem solving still heavily relies on physical modeling processes including kinematics, dynamics, or elasticity theories.

In the healthcare domain, there have been several recent attempts to infer underlying non-visual physical/physiological quantities from accessible and unobtrusive vision signals. In Poh, McDuff, and Picard (2010), heart rate, respiration rate, and heart rate variability are measured via a webcam. Authors in Ostadabbas et al. (2015) used a Kinect depth camera to measure lung function and severity of airway obstruction in patients with active obstructive pulmonary diseases. In Murthy et al. (2009), during polysomnography, thermal imaging was employed to monitor the airflow to detect potential apnea and hypopnea. The thermal modality has also been introduced for high temperature (i.e. fever) detection from faces in Nguyen et al. (2010).

There are existing computer vision tasks that are formulated in this fashion or a similar way either by focusing on regression accuracy or visual appeal. An example is human pose estimation, where an Xdomain is an RGB image from the human body and a Y domain is the body joint confidence map. Particularly in this problem, the joint coordinate regression problem is transferred to a maximum localization problem of the confidence maps which is regressed in a dense manner. See Cao et al. (2018); Wei et al. (2016). A similar yet different application is semantic segmentation. See Long, Shelhamer, and Darrell (2015), in which the X domain is an RGB image and the Y domain is its semantically segmented image, which could be seen as a pixel-wise classification problem. Another example of dense regression is image restoration, where high quality images (Y domain) are recovered from degenerated ones (X domain), including de-noising, super resolution, and de-blocking. See Tai et al. (2017). Beyond exact regression, estimating (generating) a new image from a given image/map is also similar to an image translation task via generative adversarial network (GAN) oriented models, see Zhu et al. (2017), where instead of exact recovery of the ground truth (X domain), they seek for visual pleasantness of the translated image (Y domain) with preferred "styles".

However, these existing works are proposed under their specific contexts, and they have never been tested in a contact pressure estimation context. In the case of human pose estimation, confidence map regression is just a byproduct of the algorithm and not the end goal, and the correct maximum localization is not equivalent to the quality of the generated heatmap itself, which is a surjective mapping. In image restoration examples, the inference is based on degenerated data in the same domain that is very similar to the original high quality image, which means the distance between X and Y domains is short. This characteristic is well-employed for problem solving in related studies, where instead of a total remapping, image restoration can be solved more effectively in a residue learning process. See Tai et al. (2017); Zhang et al. (2018). Even in the case of models such as GeoNet, which is a dense regression of depth and optical flow from RGB sequence, see (Yin and Shi 2018), a depth image is still a neighboring domain of its RGB image counterpart and shares strong profile with the input frame, which is employed in the GeoNet model supervision. However, to estimate dense non-vision physical properties from an image, the mapping is often between two fully distinct domains that differ not only in patterns but overall profiles. Moreover, GAN-based image generation approaches do not pursue pixel-wise accuracy and the discrimination loss is only based on visual plausibility of the generated maps and even encourage diversity in this process. See Salimans et al.

(2016). Such a 1-to-n mapping process essentially contradicts with a unique regression (1-to-1 mapping) purpose.

SUMMARY

Computer vision has achieved great success in interpreting semantic meanings from images, yet estimating underlying (non-visual) physical properties of an object is often limited to their bulk values rather than reconstructing a dense map. The technology described herein provides a pressure eye (sometimes termed "PEye") approach to estimate contact pressure between a human body and the surface she is lying on with high resolution from vision signals directly. PEye approach can enable the prediction and early detection of pressure ulcers in bed-bound patients, that currently depend on the use of expensive pressure mats. The PEye network is configured in a dual encoding shared decoding form to fuse visual cues and some relevant physical parameters in order to reconstruct high resolution pressure maps (PMs). The technology also includes a pixel-wise resampling approach based on Naive Bayes assumption to further enhance the PM regression performance. A percentage of correct sensing (PCS) tailored for sensing estimation accuracy evaluation is also provided, which provides another perspective under varying error tolerance. The approach has been via a series of experiments, in which the people's high resolution contact pressure data while lying on a bed was estimated from their RGB or long wavelength infrared (LWIR) images with 91.8% and 91.2% estimation accuracies in $PCS_{efs0.1}$ criteria, superior to state-of-the-art methods in related image regression/translation tasks.

One area that significantly benefits from automatic in-bed behavior monitoring is pressure ulcer (also known as bedsore) prevention and early detection studies in bed-bound patients. Pressure ulcers are extremely costly to treat and may lead to several other health problems, including death. Currently, the in-bed contact pressure monitoring systems mainly rely on the use of commercially available pressure mats, which are expensive and hard to maintain. The technology described herein provides contact-less pressure eye (PEye) approach that employs vision signals to infer high resolution contact pressure between human body and its lying surface.

The technology provides a pretrained model that is ready to use. The technology can be used to estimate the pressure from an image. The technology can monitor by: (1) install a webcam or IR camera on a ceiling to have a bird's eye view, (2) process the images to estimate the contact pressure.

The PEye technology can avoid the sophisticated mechanical modeling of the contact pressure and solves the problem in an end-to-end manner. The PEye network is formed with multi-stage dual encoding, shared decoding structure with both visual and non-visual physical inputs, and can enforce physical law during supervision. Besides the conventional visual modality, the RGB, the PEye approach is also evaluated when the vision signal is based on the long wavelength IR (LWIR) imaging. LWIR stays effective consistently even under complete darkness, which enables long-term in-bed behavior monitoring throughout the day with varying or no illumination states.

The technology can provide a number of advantages, including compared to existing pressure map-based approaches, the vision-based no-contact solution benefits from: (1) non-contact; (2) easy to maintain; (3) low cost; (4) functional with different modalities; (5) accurate enough to localize pressure concentration area. The technology can be used with applications for patient monitoring and for prevention of pressure related syndromes such as pressure ulcers. The technology can be used for pressure causal studies via inferred pressure distribution from the visual signal. The technology can provide sufficient accuracy to localize pressure concentrated area, resulting in a smaller size, cheaper price and convenience of maintenance than a direct pressure measurement system.

In one aspect, a system for estimating contact pressure of a human lying on a surface is provided. The system includes one or more imaging devices oriented toward a surface, the imaging devices comprising one or more imaging sensors. The system also includes a processor and memory, including a trained model for estimating human contact pressure trained with a dataset comprising a plurality of human lying poses comprising images generated from at least one of a plurality of imaging modalities, the plurality of imaging modalities including at least one of a red-green-blue (RGB) imaging modality, a long wavelength infrared (LWIR) imaging modality, a depth imaging modality, or a pressure map imaging modality. The processor is in communication with the one or more imaging devices to receive one or more images of a human lying on the surface and a source of one or more physical parameters of the human lying on the surface and is operative to determine a pressure map of the human lying on the surface based on the one or more images of a human lying on the surface and the one or more physical parameters of the human lying on the surface.

In some embodiments, the processor is operative to encode signals representing the images of the human lying on the surface and the physical parameters of the human lying on the surface separately, concatenate the encoded signals, and decode the signals jointly. In some embodiments, the dataset further comprises one or more physical parameters corresponding to a human subject of each image of each set of images. In some embodiments, the source of the one or more physical parameters is at least one of a memory storing patient information, a scale positioned on or integrated into the surface, a pressure mat positioned on or integrated into the surface, or an image processing module. In some embodiments, the one or more imaging devices includes at least one of a camera, a video camera, an infrared camera, an infrared video camera, a depth camera, a CCD sensor, a CMOS sensor, an infrared sensor, a depth sensor, a structural light sensor, a time of flight sensor, a camera array, a LIDAR scanner, a 3D camera, or combinations thereof. In some embodiments, the surface is at least one of a hospital bed, a residential bed, a surgical table, a cot, a gurney, a floor of a kennel or crate for animal use, or a crib or bassinet.

In another aspect, a method is provided for estimating contact pressure of a human lying on a surface. The method includes providing a processor and memory, including a trained model for estimating human contact pressure trained with a dataset comprising a trained model for estimating human contact pressure trained with a dataset comprising a plurality of human lying poses comprising images generated from at least one of a plurality of imaging modalities, the plurality of imaging modalities including at least one of a red-green-blue (RGB) imaging modality, a long wavelength infrared (LWIR) imaging modality, a depth imaging modality, or a pressure map imaging modality. The method also incldues receiving at the processor one or more images of a human lying on a surface from one or more imaging devices oriented toward the surface, the imaging devices comprising one or more imaging sensors. The method also includes receiving at the processor one or more physical parameters of the human lying on the surface from a physical parameter source. The method also includes generating a contact pressure map of the human lying on the surface based on the one or more images of a human lying on the surface and the one or more physical parameters of the human lying on the surface.

In some embodiments, the processor is operative to encode signals representing the images of the human lying on the surface and the one or more physical parameters of the human lying on the surface separately, concatenate the encoded signals, and decode the signals jointly. In some embodiments, the method also includes generating the dataset of the plurality of human lying poses by gathering images of the human lying poses according to at least one of the plurality of imaging modalities, the modalities including at least one of the red-green-blue (RGB) imaging modality, the long wavelength infrared (LWIR) imaging modality, the depth imaging modality, or the pressure map imaging modality. In some embodiments, the method also includes labeling the poses. In some embodiments, the method also incldues storing the gathered images as labeled poses in a database. In some embodiments, the method also includes training a model for estimating contact pressure of a human lying on a surface with the dataset.

In some embodiments, the model can be expressed as $L_{total} = \lambda_{pwrs} L_{2\text{-}1}^{pwrs} + \lambda_{phy} L_2^{phy}$. In some embodiments, $L_{2\text{-}1}^{pwrs} = \lambda_{L_2} \Sigma_{i=0}^{M} \Sigma_{j=0}^{N} (\hat{y}(i,j) - y(i,j))^2 (1/p(y(i,j)+\xi))$. In some embodiments, $L_2^{phy} = (c\Sigma_i \Sigma_j \hat{y}(i,j) - w_b)^2$. In some embodiments, $L_{2\text{-}1}^{pwrs}$ is a pixel-wise resampling (PWRS) loss. In some embodiments, $L_2^{phy}$ is a physical loss. In some embodiments, $\lambda_{pwrs}$ and $\lambda_{phy}$ stand for the weights applied to each loss term, respectively. In some embodiments, y(i, j) represents a pixel value at i and j coordinates of a pressure map. In some embodiments, s(y(i, j)) is a function defined to map the specific pressure map pixel value into a corresponding resample number. In some embodiments, M is a row size of the pressure map. In some embodiments, N is a column size of the pressure map. In some embodiments, $w_b$ stands for the human's body weight. In some embodiments, c is a contact area with the bed represented by each pixel of the pressure map.

In some embodiments, the physical parameters include one or more of weight, height, gender, bust, waist, hip, upper arm circumference, lower arm circumference, thigh circumference, and shank circumference. In some embodiments, the dataset also includes one or more physical parameters corresponding to a human subject of each image of each set of images. In some embodiments, the method also includes correlating one or more physical parameters corresponding to a human subject of each of the gathered images to a corresponding one of the labeled poses in the database. In some embodiments, the method also includes transmitting instructions to a medical professional device for repositioning a patient to a different posture. In some embodiments, the different posture is determined according to a posture scheduling algorithm. In some embodiments, the surface is a repositionable bed and the method further comprises transmitting instructions to the repositionable bed for repositioning a patient to a different posture.

In another aspect, a method for generating a dataset of a plurality of human lying poses is provided. The method includes gathering images of human lying poses according to at least one of a plurality of imaging modalities, the plurality of imaging modalities including at least one of a red-green-blue (RGB) imaging modality, a long wavelength infrared (LWIR) imaging modality, a depth imaging modality, or a pressure map imaging modality. The method also includes labeling the poses. The method also includes storing the gathered images as labeled poses in a database.

In some embodiments, the method also inlcudes correlating one or more physical parameters corresponding to a human subject of each of the gathered images to a corresponding one of the labeled poses in the database.

In another aspect, a method for estimating contact pressure of a human lying on a surface is provided. The method includes generating a dataset of the plurality of human lying poses, comprising gathering images of human lying poses from at least one of a plurality of imaging modalities, the plurality of imaging modalities including at least one of a red-green-blue (RGB) imaging modality, a long wavelength infrared (LWIR) imaging modality, a depth imaging modality, or a pressure map imaging modality. The method also includes training a model for estimating contact pressure of a human lying on a surface with the dataset.

In some embodiments, the model can be expressed as $L^{total} = \lambda_{pwrs} L_{2\text{-}1}^{pwrs} + \lambda_{phy} L_2^{phy}$. In some embodiments, $L_{2\text{-}1}^{pwrs} = \lambda_{L_2} \Sigma_{i=0}^{M} \Sigma_{j=0}^{N} (\hat{y}(i,j) - y(i,j))^2 (1/p(y(i,j)+\xi))$. In some embodiments, $L_2^{phy} = (c\Sigma_i \Sigma_j \hat{y}(i,j) - w_b)^2$. In some embodiments, $L_{2\text{-}1}^{pwrs}$ is a pixel-wise resampling (PWRS) loss. In some embodiments, $L_2^{phy}$ is a physical loss. In some embodiments, $\lambda_{pwrs}$ and $\lambda_{phy}$ stand for the weights applied to each loss term, respectively. In some embodiments, y(i, j) represents a pixel value at i and j coordinates of a pressure map. In some embodiments, s(y(i, j)) is a function defined to map the specific pressure map pixel value into a corresponding resample number. In some embodiments, M is a row size of the pressure map. In some embodiments, N is a column size of the pressure map. In some embodiments, $w_b$ stands for the human's body weight. In some embodiments, c is a contact area with the bed represented by each pixel of the pressure map.

Additional features and aspects of the technology include the following:

1. A system for estimating contact pressure of a human lying on a surface, comprising:
    one or more imaging devices oriented toward a surface, the imaging devices comprising one or more imaging sensors; and
    a processor and memory, including a trained model for estimating human contact pressure trained with a dataset comprising a plurality of human lying poses comprising images generated from at least one of a plurality of imaging modalities, the plurality of imaging modalities including at least one of a red-green-blue (RGB) imaging modality, a long wavelength infrared (LWIR) imaging modality, a depth imaging modality, or a pressure map imaging modality;
    wherein the processor is in communication with the one or more imaging devices to receive one or more images of a human lying on the surface and a source of one or more physical parameters of the human lying on the surface and is operative to determine a pressure map of the human lying on the surface based on the one or more images of a human lying on the surface and the one or more physical parameters of the human lying on the surface.
2. The system of claim 1, wherein the processor is operative to encode signals representing the images of the human lying on the surface and the physical parameters of the human lying on the surface separately, concatenate the encoded signals, and decode the signals jointly.

3. The system of any of claims 1-2, wherein the dataset further comprises one or more physical parameters corresponding to a human subject of each image of each set of images.

4. The system of any of claims 1-3, wherein the source of the one or more physical parameters is at least one of a memory storing patient information, a scale positioned on or integrated into the surface, a pressure mat positioned on or integrated into the surface, or an image processing module.

5. The system of any of claims 1-4, wherein the one or more imaging devices includes at least one of a camera, a video camera, an infrared camera, an infrared video camera, a depth camera, a CCD sensor, a CMOS sensor, an infrared sensor, a depth sensor, a structural light sensor, a time of flight sensor, a camera array, a LIDAR scanner, a 3D camera, or combinations thereof 6. The system of any of claims 1-5, wherein the surface is at least one of a hospital bed, a residential bed, a surgical table, a cot, a gurney, a floor of a kennel or crate for animal use, or a crib or bassinet.

7. A method for estimating contact pressure of a human lying on a surface comprising:
providing a processor and memory, including a trained model for estimating human contact pressure trained with a dataset comprising a trained model for estimating human contact pressure trained with a dataset comprising a plurality of human lying poses comprising images generated from at least one of a plurality of imaging modalities, the plurality of imaging modalities including at least one of a red-green-blue (RGB) imaging modality, a long wavelength infrared (LWIR) imaging modality, a depth imaging modality, or a pressure map imaging modality, and
receiving at the processor one or more images of a human lying on a surface from one or more imaging devices oriented toward the surface, the imaging devices comprising one or more imaging sensors;
receiving at the processor one or more physical parameters of the human lying on the surface from a physical parameter source; and
generating a contact pressure map of the human lying on the surface based on the one or more images of a human lying on the surface and the one or more physical parameters of the human lying on the surface.

8. The method of claim 7, wherein the processor is operative to encode signals representing the images of the human lying on the surface and the one or more physical parameters of the human lying on the surface separately, concatenate the encoded signals, and decode the signals jointly.

9. The method of any of claims 7-8, further comprising generating the dataset of the plurality of human lying poses by gathering images of the human lying poses according to at least one of the plurality of imaging modalities, the modalities including at least one of the red-green-blue (RGB) imaging modality, the long wavelength infrared (LWIR) imaging modality, the depth imaging modality, or the pressure map imaging modality.

10. The method of claim 9, further comprising:
labeling the poses; and
storing the gathered images as labeled poses in a database.

11. The method of claim 10, further comprising training a model for estimating contact pressure of a human lying on a surface with the dataset.

12. The method of claim 11, wherein the model can be expressed as:

$$L^{total} = \lambda_{pwrs} L_{2-1}^{pwrs} + \lambda_{phy} L_2^{phy};$$

wherein $$L_{2-1}^{pwrs} = \lambda_{L_2} \sum_{i=0}^{M} \sum_{j=0}^{N} (\hat{y}(i,j) - y(i,j))^2 (1/p(y(i,j) + \xi));$$

wherein $$L_2^{phy} = \left( c \sum_i \sum_j \hat{y}(i,j) - w_b \right)^2;$$

wherein $L_{2-1}^{pwrs}$ is a pixel-wise resampling (PWRS) loss;
wherein $L_2^{phy}$ is a physical loss;
wherein $\lambda_{pwrs}$ and $\lambda_{phy}$ stand for the weights applied to each loss term, respectively;
wherein y(i, j) represents a pixel value at i and j coordinates of a pressure map;
wherein s(y(i, j)) is a function defined to map the specific pressure map pixel value into a corresponding resample number;
wherein M is a row size of the pressure map;
wherein N is a column size of the pressure map;
wherein $w_b$ stands for the human's body weight; and
wherein c is a contact area with the bed represented by each pixel of the pressure map.

13. The method of any of claims 7-12, wherein the physical parameters include one or more of weight, height, gender, bust, waist, hip, upper arm circumference, lower arm circumference, thigh circumference, and shank circumference.

14. The method of any of claims 7-13, wherein the dataset further comprises one or more physical parameters corresponding to a human subject of each image of each set of images.

15. The method of claim 10, further comprising correlating one or more physical parameters corresponding to a human subject of each of the gathered images to a corresponding one of the labeled poses in the database.

16. The method of any of claims 7-15, further comprising transmitting instructions to a medical professional device for repositioning a patient to a different posture.

17. The method of claim 16, wherein the different posture is determined according to a posture scheduling algorithm.

18. The method of any of claims 7-17, wherein the surface is a repositionable bed and the method further comprises transmitting instructions to the repositionable bed for repositioning a patient to a different posture.

19. A method for generating a dataset of a plurality of human lying poses, comprising:
gathering images of human lying poses according to at least one of a plurality of imaging modalities, the plurality of imaging modalities including at least one of a red-green-blue (RGB) imaging modality, a long wavelength infrared (LWIR) imaging modality, a depth imaging modality, or a pressure map imaging modality;
labeling the poses; and
storing the gathered images as labeled poses in a database.

20. The method of claim 19, further comprising correlating one or more physical parameters corresponding to a human subject of each of the gathered images to a corresponding one of the labeled poses in the database.

21. A method for estimating contact pressure of a human lying on a surface, comprising:
   generating a dataset of the plurality of human lying poses, comprising gathering images of human lying poses from at least one of a plurality of imaging modalities, the plurality of imaging modalities including at least one of a red-green-blue (RGB) imaging modality, a long wavelength infrared (LWIR) imaging modality, a depth imaging modality, or a pressure map imaging modality; and
   training a model for estimating contact pressure of a human lying on a surface with the dataset.
22. The method of claim 21, wherein the model can be expressed as:

$$L^{total} = \lambda_{pwrs} L_{2-1}^{pwrs} + \lambda_{phy} L_2^{phy};$$

wherein $$L_{2-1}^{pwrs} = \lambda_{L_2} \sum_{i=0}^{M} \sum_{j=0}^{N} (\hat{y}(i,j) - y(i,j))^2 (1/p(y(i,j) + \xi));$$

wherein $$L_2^{phy} = \left( c \sum_i \sum_j \hat{y}(i,j) - w_b \right)^2;$$

wherein $L_{2-l}^{pwrs}$ is a pixel-wise resampling (PWRS) loss;
wherein $L_2^{phy}$ is a physical loss;
wherein $\lambda_{pwrs}$ and $\lambda_{phy}$ stand for the weights applied to each loss term, respectively;
wherein y(i, j) represents a pixel value at i and j coordinates of a pressure map;
wherein s(y(i, j)) is a function defined to map the specific pressure map pixel value into a corresponding resample number;
wherein M is a row size of the pressure map;
wherein N is a column size of the pressure map;
wherein $w_b$ stands for the human's body weight; and
wherein c is a contact area with the bed represented by each pixel of the pressure map.

DESCRIPTION OF THE DRAWINGS

Reference is made to the following detailed description taken in conjunction with the accompanying drawings in which:

FIG. 7B illustrates performance of PEye network with pwrs-phy configuration with different physical vector β when input domain is RGB zoomed-in.

FIG. 7D illustrates performance of PEye network with pwrs-phy configuration with different physical vector β when input domain is LWIR zoomed-in.

FIGS. 11G-L illustrate SLP image data samples from in-bed supine and side postures showing images captured using an LWIR camera. These images are taken from the participants without cover (FIGS. 11G, 11J), with a thin cover (FIGS. 11H, 11K), and with a thick cover (FIGS. 11I, 11L).

FIG. 13 illustrates turning schedules for each subject and patient condition scenario.

DETAILED DESCRIPTION

Figure 1:
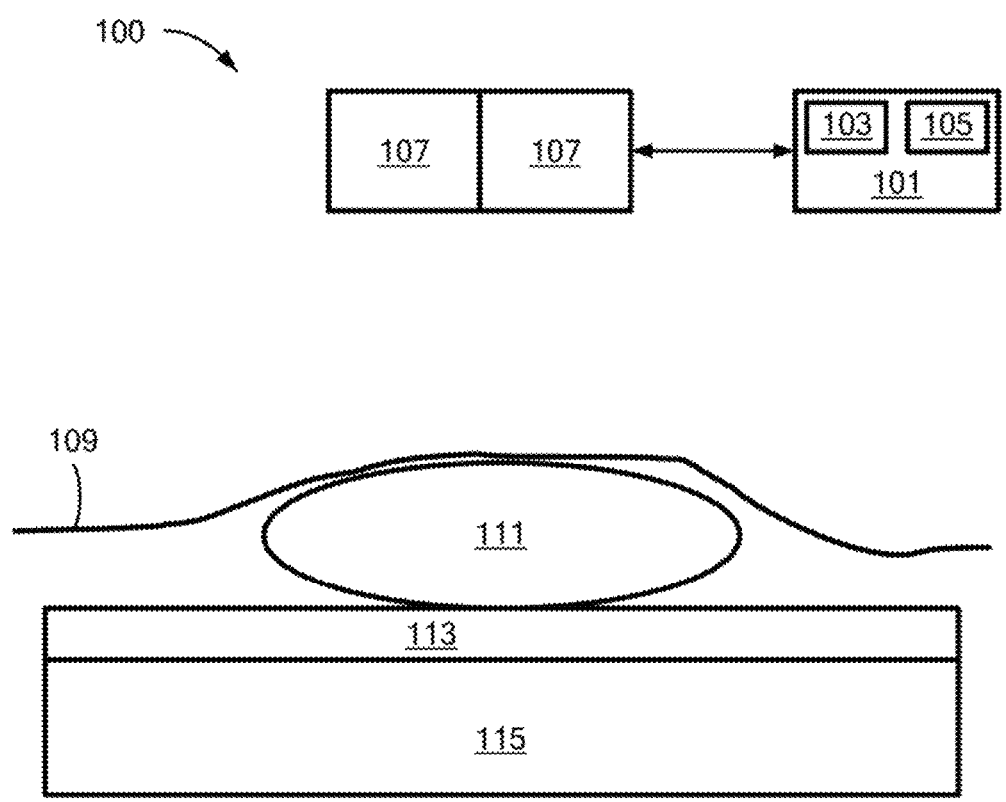
FIG. 1 is a schematic diagram of a pressure eye (PEye) multimodal data collection setup in accordance with various embodiments.

The technology described herein provides a contact-less pressure eye (PEye) approach that employs vision signals to infer high resolution contact pressure between human body and its lying surface. The technology can provide a dense map of in-bed contact pressure based on its correspondence to the vision field, in contrast to prior art work, which focuses on estimating the bulk physical properties such as weight or total force, rather than providing a dense map of the physical quantity of interest. The technology can take into consideration not only the visual cues but also pressure-related physical quantities as the inputs and regress them directly to estimate the contact pressure. By employing deep neural network learning capabilities, PEye avoids the sophisticated mechanical modeling of the contact pressure and solves the problem in an end-to-end manner. The PEye network is formed with multi-stage dual encoding, shared decoding structure with both visual and non-visual physical inputs, and the technology enforces physical law during supervision. Besides the conventional visual modality, the RGB, the PEye approach is also evaluated when the vision signal is based on the long wavelength IR (LWIR) imaging. LWIR stays effective consistently even under complete darkness, which enables long-term in-bed behavior monitoring throughout the day with varying and/or no illumination states.

There is no existing work to estimate dense pressure map (PM) directly from a vision signal. The problem can be formulated in the abstract as, given an image X in domain A, inferring its underlying physical quantity map, Y in domain B can mathematically be represented as a dense regression problem, $Y=\varphi(X)$. However, the following concerns still exist with attempting to solve PM estimations based on its regression-based nature. First, having an image/map X is not always sufficient to estimate a physical quantity Y. In a working example, suppose there are two similar size/color cubes on a surface but with different weights (e.g. iron vs. plastic). While, they look visually similar, their contact pressure is vastly different. Therefore, additional physical property is needed to solve the problem, for example providing the material types. In that case, the inference is based on both visual and non-visual signals, instead of X, alone. Secondly, while at first glance PM looks like a style-differed image (see FIG. 4C), there is a "long" domain difference between the visual input and the non-visual PM. Looking closer at the FIG. 4C, it is apparent that although X and Y have a similar pose, they are not sharing the same profile.

Pressure Map Estimation Technology Summary

In contrast to the above mentioned works, pressure map (PM) estimation is a regression problem, in which pixel-wise accuracy is required. Moreover, due to its medical "decision support" nature, the distribution patterns should be presented accurately in order to correctly identify high pressure concentration areas. Compared to a direct translation, PM estimation is more like a data-driven solver that takes the visual clues from RGB or LWIR images and solves the contact pressure mechanics problem in an end-to-end manner with high resolution. The PEye approach of the technology herein can address the specific context and concerns around the PM estimation task, and provides improvements over the existing regression-based approaches to achieve better in-bed contact pressure estimation.

The pressure map estimation technology described herein provides design and implementation of the PEye network in a dual encoding shared decoding form to fuse the visual cues and the relevant physical measures in order to reconstruct a high resolution PM of a person in a given in-bed position. Based on a Naive Bayes assumption, a pixel-wise resampling (PWRS) approach is described to enhance the peak value recovery in sparse PM profiles. The technology provides an evaluation metric to measure pressure sensing performance. Standard metrics for regression problems, either mean square error (MSE) or peak signal-to-noise ratio (PSNR) only provide an overview of the reconstruction results; the technology herein provides a percentage correct sensing (PCS) metric, which provides another perspective on how a "sensing array" performs under varying error tolerance. The technology provides a large in-bed multimodal human pose dataset with >100 human subjects with nearly 15,000 pose images including RGB, LWIR, and contact pressure map.

Pressure Eye (PEye) Technology

Referring now to FIG. 1, a schematic diagram of a pressure eye (PEye) multimodal data collection setup is provided. The PEye system 100 includes a computing device 101 having a processor 103 and a memory 105, The computing device 101 is in electronic communication with one or more imaging devices 107 for receiving one or more images of a subject 111 positioned on a surface 115. In some embodiments, the subject 111 can be covered with one or more covers 109 for warmth and/or comfort. In some embodiments, a physical parameter sensor 113 may be provided interposed between the subject 111 and the surface 115 (or integrated into the surface 115) to provide a source of one or more physical parameters of the subject 111.

The computer 101 can be any suitable computing device capable of executing the one or more of the various methods, operations, modules, and systems described herein for estimating contact pressure of a human lying on a surface from imaging data may. The computer 101 can include the processor 103 (e.g., a microprocessor, a field-programmable gate array (FPGA), or any other suitable processor capable of processing instructions stored in the memory 105), the memory 105 (e.g., random access memory, read-only memory, a hard disk drive, a solid-state storage device, an optical disk device) readable by the processor 103. The computer 101 can also include additional components (not shown) such as, for example, input/output devices (e.g., a display, keyboard, pointer device, etc.) and/or a graphics module for generating graphical objects.

The one or more imaging devices 107 can include, for example at least one of a camera, a video camera, an infrared camera, an infrared video camera, a CCD sensor, a CMOS sensor, an infrared sensor, a depth sensor, a LIDAR scanner, a 3D camera, or combinations thereof. In general, the imaging devices 107 can be directed to collect imaging data including the subject 111.

The subject 111 can generally be any human or veterinary patient. The bed 115 or other surface can include, for example, a hospital bed, a residential bed, a gurney, a cot, a surgical table, a crib or bassinet, a floor of a kennel or crate for animal use, or combinations thereof.

The physical parameter sensor 113 can include, for example, a pressure mat positioned on or integrated into the surface, a weight scale or sensor positioned on or integrated into the surface, or combinations thereof. In some embodiments, physical parameters can instead or additionally be obtained by other physical parameter sensors such as, for example, an image processing module (not shown) of the computer 101, known information about the subject stored in the memory 105, combinations thereof, or any other suitable source of physical parameter data corresponding to the subject 111.

Figure 2:
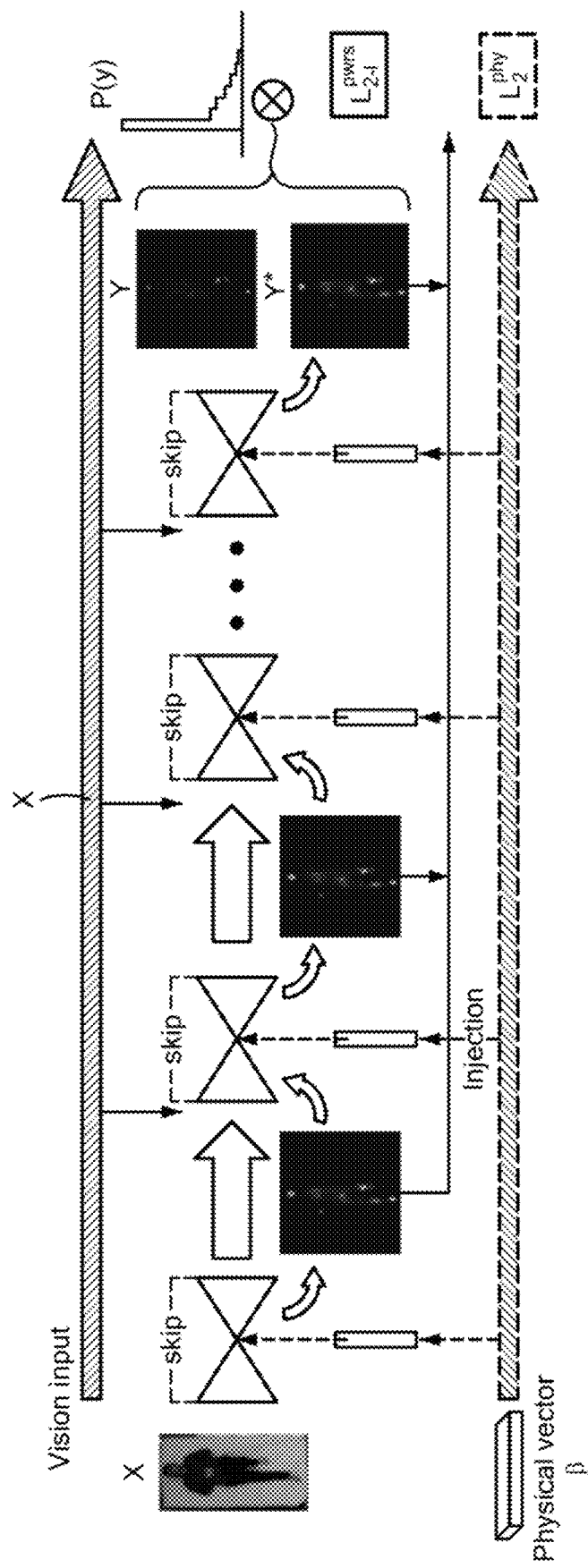
FIG. 2 is a schematic illustration of a PEye network structure for in-bed contact pressure estimation in accordance with various embodiments.

The PEye approach takes RGB and/or LWIR images as its source domain and generates pressure map (PM) signals as its target domain, as shown in FIG. 2. Estimating the contact pressure using only a vision signal is an ill-posed problem, as RGB or LWIR cannot correctly represent pressure maps of objects with similar appearance but different densities. Furthermore, the differences in human body shapes/geometries lead to different pressure distributions on bed. Therefore, besides a vision signal (RGB or LWIR), a physical vector β is fed into the PEye network, which incorporates several physique parameters from the human participants, including their body weight, gender, and their anthropometric measurements (e.g., tailor measurements). The details of such physique parameters are discussed in greater detail below.

Figure 3:
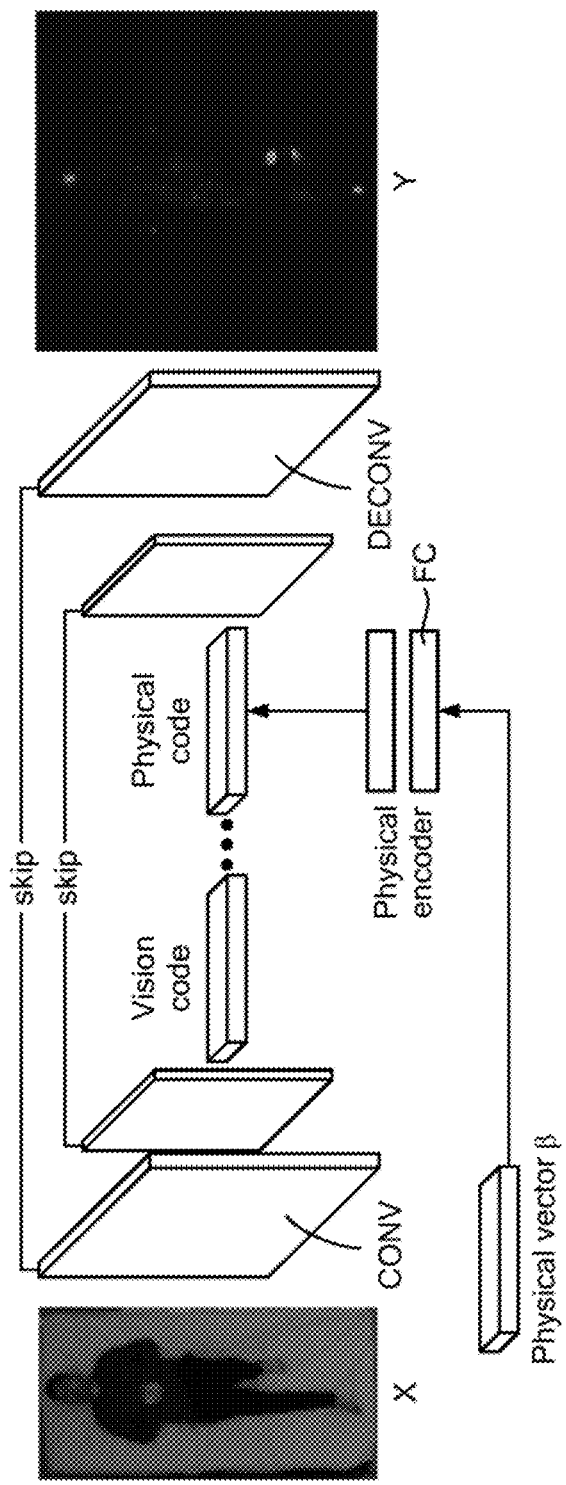
FIG. 3 is a schematic illustration of an overview of the PEye network building blocks in accordance with various embodiments.

The PEye network has a multi-stage design by stacking multiple building modules. Each module has a skipped encoding-decoding structure. To feed in the physical vector β, additional reconfiguration is applied, such that a physical encoder is added to form a dual encoding, shared decoding structure. The vision signal X and the physical measures β are encoded separately, then concatenated and decoded jointly as shown in FIG. 3. The decoding process turns out to be based on the merged code of both vision and physical vectors. The convolution and deconvolution layers are both followed by the reLU and batch normalization layers.

Figure 4A:
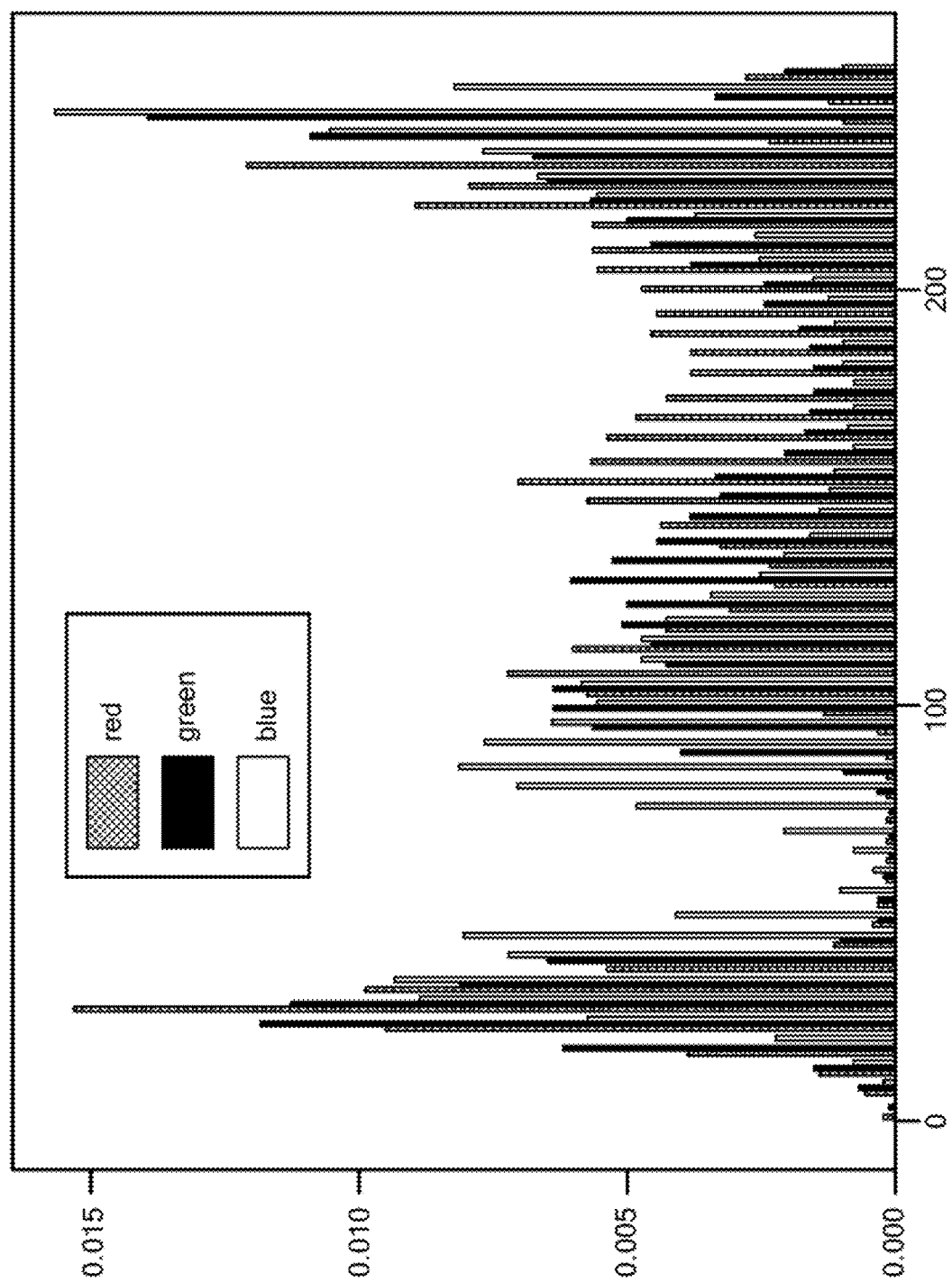
FIG. 4A is a histogram of RGB images shown in FIG. 4C.
Figure 4B:
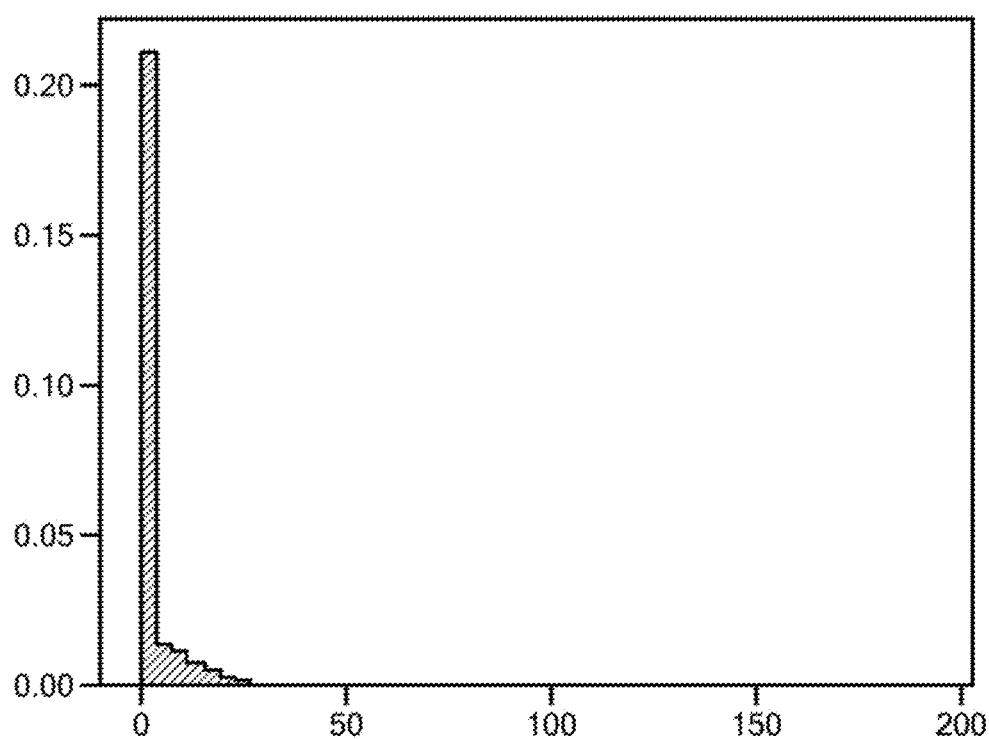
FIG. 4B is a histogram comparison of pressure map (PM) images shown in FIG. 4C.
Figure 4C:
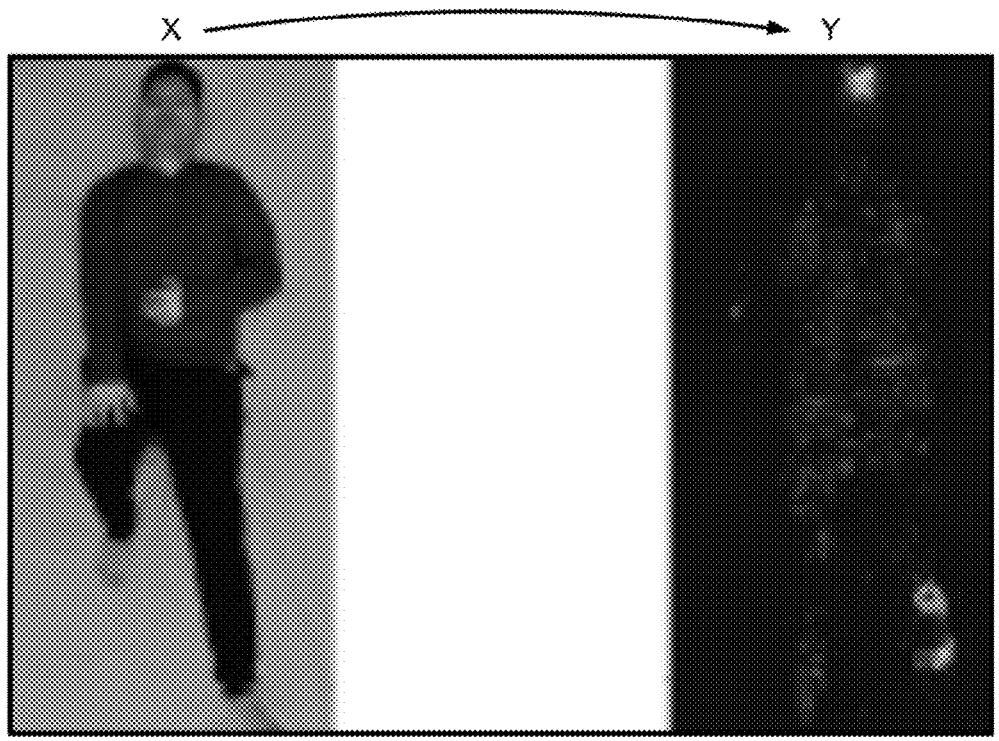
FIG. 4C is a depiction of a non-contact, in-bed pressure estimation image generation task undertaken using the present pressure eye (PEye) approach in accordance with various embodiments.

Looking at the PM samples in the dataset, compared to an RGB image, as shown in FIG. 4C, PM looks quite different in style. Specifically, PM looks more simple, unfilled, with several hollow areas. PM is also unevenly distributed and concentrated only on a very few supportive areas such as hips and shoulders that generate sharp peaks. Therefore, many PM pixels are in a low value range with only a very few in a high value range. This can be quantitatively reflected in the histogram comparison of an RGB image and its PM counterpart, as shown in FIGS. 4A-4B. An immediate question is if the PM value distribution imbalance would affect the performance of the pressure regression task.

Pixel-Wise Resampling (PWRS)

Techniques used to address data imbalance issues in machine learning (ML) for classification problems can be applied in the present technology. In a binary classification problem, class imbalance occurs when one class, the minority group, contains significantly fewer samples than the other class, the majority group. In many problems, the minority group is the class of higher interest, i.e. the positive class. This is also the present case, in which the high pressure concentrated areas of present interest turn out to be the minority, as the histogram in FIG. 4B shows. Although most existing methods for imbalanced data focus on the classification problems, these techniques can be introduced into a regression task, such as the resampling strategy. The purpose of resampling is to make each "class" presented in the task with equivalent quantities during training. One way is oversampling the underrepresented class by multiple times to make each class relatively equal in size.

To do this in the present case, one immediate solution is to collect PMs with more readings within high range values. However, in the context of in-bed pressure mapping, this is challenging since high pressure values are mainly concentrated in a small number of supporting areas. To simplify this problem, similar to Naive Bayes approach, the PM pixel values are assumed to be independent. So, the PM resampling is simplified into the pixel-wise resampling (PWRS) with a trade-off between the accuracy and sampling feasibility. As the resample number (RSN) depends on the specific PM value y(i, j) at i and j coordinates, a function s(y(i, j)) is defined, which maps the pixel value into the corresponding RSN. A typical $L_2$ loss after resampling becomes:

$$L_2^{pwrs} = \sum_{i=0}^{M}\sum_{j=0}^{N}\sum_{k=0}^{s(y(i,j))}(\hat{y}(i,j) - y(i,j))^2 = \sum_{i=0}^{M}\sum_{j=0}^{N}s(y(i,j))(\hat{y}(i,j) - y(i,j))^2 \quad (1)$$

where M and N stand for the row and column size of the PM, and ŷ stands for the estimated PM result. If s(y(i, j) is simply deemed as weight, it is not necessary to be an integer and the resampling of each pixel can be a pixel-wise weighted $L_2$ loss. One way to build RSN function s is making it inversely proportional to the density function of the pixel value y, such that $s(y)=\lambda_{L2}/p(y)$, where $\lambda_{L2}$ is a constant and p(y) is the density function of y. Then, the PWRS loss is formulated as:

$$L_2^{pwrs} = \lambda_{L_2}\sum_{i=0}^{M}\sum_{j=0}^{N}(\hat{y}(i,j) - y(i,j))^2/p(y(i,j)) \quad (2)$$

The PM pixel values in high pressure range are highly sparse. One typical solution is using Laplace smoothing by adding evenly distributed additional "hallucinated" examples. A hallucinated weight ξ is added instead to enhance under weighted pixel values and have a Laplace smoothed loss as:

$$L_{2-1}^{pwrs} = \lambda_{L_2}\sum_{i=0}^{M}\sum_{j=0}^{N}(\hat{y}(i,j) - y(i,j))^2(1/p(y(i,j) + \xi)) \quad (3)$$

PEye Network Optimization

For PEye network training, in addition to the $L_{2-1}^{pwrs}$ loss, the physical loss $L_2^{phy}$ is introduced, which incorporates the dominant law in pressure forming process. Contact pressure is a sophisticated interactive process between the body parts and the support surface. Detailed modeling of this process is complex and against the end-to-end purpose of a data-driven approach. So, the technology employs the simple but dominant law for pressure forming as:

$$L_2^{phy} = \left(c\sum_{i}\sum_{j}\hat{y}(i,j) - w_b\right)^2 \quad (4)$$

where $w_b$ stands for the person's body weight, and c is the contact area with the bed represented by each PM pixel. This loss reflects that integration of pressure over the contact area should be equal to the person's total weight. As a part of the physical vector β, $w_b$ is included in both input and the loss function, which inherently shows the network how to utilize the additional physical information. With a dual encoder input, the decoder net is supervised from both visual and physical perspectives and the total loss function is given as:

$$L_{total} = \lambda_{pwrs} L_{2-1}^{pwrs} + \lambda_{phy} L_2^{phy} \quad (5)$$

where $\lambda_{pwrs}$ and $\lambda_{phy}$ stand for the weights applied to each loss term, respectively. Additional losses can be introduced to further enhance the visual plausibility of the generated maps, such as patchGAN by adversarial learning, or structural similarity index (SSIM) loss. Their effects on PM reconstruction performance are further evaluated in the ablation study.

Percentage of Correct Sensing (PCS) Metric

A way to evaluate a regression problem is calculating the overall mean square error (MSE), in which each pixel contributes evenly in the MSE calculation. However, in many sensing applications, the estimation accuracy in active sensing areas is much more important than the irrelevant background. In this case, MSE of effective area makes more sense, where the focus is only on the active sensing area. Inspired by this as well as the probability of correct keypoint (PCK) metric in human pose estimation models, the technology further provides a percentage of correct sensing (PCS) metric of effective area to provide another evaluation under varying error tolerance. Effective PCS metric is defined as:

$$PCS_{efs(\epsilon)} = \frac{|E[efs] < \epsilon|}{|E[efs]|} \quad (6)$$

where E is the error map, which is the difference between the ground truth and the estimated map, $|\cdot|$ is an element-wise counting operation (i.e. cardinality), and efs indicates a selection matrix, which specifies the effective sensing area. Threshold E could be set by a domain-specific absolute value or a normalized value based on the sensing range.

The idea behind PCS comes from the fact that for a physical sensor, as long as its estimated value is within a predefined application-specific tolerance range, it could be assumed as a qualified reading. In an array format, it is only necessary to calculate how many sensors are within this range to evaluate their performance. Otherwise, a few strong outliers can contribute substantially to a high MSE, while most of the estimated values are correct. PCS also provides a comprehensive view of the sensing performance with varying error tolerance, since different application scenarios could hold different threshold for errors. In PEye, the efs threshold is chosen to be 5% or 10% of the maximum value of the PM as the low response pixels often are the unoccupied areas or the ones of low interest in practice.

Experimental Analysis

Multimodal Dataset Collection

To evaluate PEye approach effectiveness in generating pressure data from vision signals, a dataset was formed, where RGB, LWIR and PM signals were collected using a Logitech webcam, a FLIR IR camera, and a Tekscan pressure sensing mat, respectively. Data was collected from 102 subjects that were instructed to lie down on a twin-size bed and take random poses in natural ways. To encourage pose diversity, participants were instructed to evenly give 15 poses under three rough posture categories as supine, left side, and right side. Data from 12 subjects were left out for test purpose, while the rest were used for PEye network training. During data collection, a weighted marker was used to achieve a rough cross domain data alignment via a homography mapping.

Evaluation Metrics

As a regression problem, a goal was to generate accurate dense maps of contact pressure. Therefore, both MSE over effective area MSEefs as well as the provided PCSefs metrics were reported. To provide a comprehensive evaluation, popular metrics from related tasks were also employed. For example, in image restoration task, PSNR and SSIM scores were commonly used (see Tai et al. 2017; Wang et al. 2004).

Details on Network Training

The loss weights $\lambda_{pwrs}$ and $\lambda_{phy}$ were set to 100 and 1e-06 when employed, otherwise to 0. In the ablation, the effect of the featured components were also studied in relevant tasks such as the discriminator for adversarial learning and SSIM score loss, in which they were given weights of 1 and 10 respectively, when used. For configuration with discriminator, a 3-layer PatchGAN structure as presented in (Ledig et al. 2017) was employed.

The input and output data were normalized to [0, 1] interval according to their dynamic range. For each network configuration, 30 epochs and 0.0002 learning rate with Adam solver (Kingma and Ba 2014) were used. For the last 5 epochs, learning rate was linearly decayed. As suggested in (Brock, Donahue, and Simonyan 2018), the largest batch size based on the available computational resources during training was employed, which was 70 for the PEye network. All models were implemented under pyTorch framework. Training and testing were conducted on a single NVIDIA V100 GPU.

Ablation Study

Here, how PWRS and the introduced physical constraint affect the PEye model's performance were explored. It was also interesting to investigate how the featured components/supervision in other similar tasks affected PEye performance. This included the adversarial training strategy (represented as $L_D$ loss) for realistic image generation and the SSIM score for structural similarity (represented as $L_{ssim}$ loss).

First, a model was implemented with all necessary inputs including the visual image X and the physical vector $\beta$ containing body weight (based on Eq. (4)). How the additional physical parameters affected the model performance were further explored in the Supplementary Materials. The conventional $L_2$ reconstruction loss was employed during the supervision, which specifically focused on minimizing the MSE. This first model called "base" formed a typical regression problem similar to the most regression tasks focusing only on a $L_2$ loss, for example the human pose estimation (Sun et al. 2019; Newell, Yang, and Deng 2016). Based on this, components were gradually added including PWRS strategy, body weight constraint, and also $L_D$ and $L_{ssim}$ losses to study how they affect the model's performance. In the ablation study, components were evaluated individually as well as jointly. The same ablation was conducted for both RGB and LWIR respectively as the input X

TABLE 1

Performance of different PEye network configurations with RGB as input image modality.

| | Metrics | | | | |
|---|---|---|---|---|---|
| Models | $MSE_{efs}$(e-3) | PSNR | $PCSefs0.05$ | $PCSefs0.1$ | SSIM |
| base | 9.04 | 80.76 | 0.360 | 0.839 | 0.956 |
| pwrs | 5.22 | 75.36 | 0.673 | 0.910 | 0.919 |
| pwrs-phy | 4.80 | 73.36 | 0.707 | 0.918 | 0.906 |
| pwrs-phy-ssim | 8.83 | 79.73 | 0.498 | 0.861 | 0.959 |
| pwrs-phy-ssim-D | 8.28 | 78.60 | 0.455 | 0.852 | 0.953 |
| phy | 8.92 | 80.73 | 0.379 | 0.841 | 0.956 |
| ssim | 8.65 | 81.36 | 0.420 | 0.848 | 0.960 |
| D | 8.21 | 78.38 | 0.451 | 0.854 | 0.950 |

TABLE 2

Performance of different PEye network configurations with LWR as input image modality.

| | Metrics | | | | |
|---|---|---|---|---|---|
| Models | $MSE_{efs}$(e-3) | PSNR | $PCSefs0.05$ | $PCSefs0.1$ | SSIM |
| base | 8.90 | 81.01 | 0.359 | 0.841 | 0.957 |
| pwrs | 5.18 | 72.63 | 0.662 | 0.904 | 0.901 |
| pwrs-phy | 4.81 | 71.50 | 0.695 | 0.912 | 0.887 |
| pwrs-phy-ssim | 8.14 | 81.74 | 0.462 | 0.859 | 0.962 |
| pwrs-phy-ssim-D | 8.02 | 78.85 | 0.469 | 0.859 | 0.954 |
| phy | 8.78 | 81.14 | 0.375 | 0.845 | 0.957 |
| ssim | 8.29 | 81.68 | 0.447 | 0.856 | 0.962 |
| D | 7.85 | 78.06 | 0.483 | 0.862 | 0.949 |

Figure 5A:
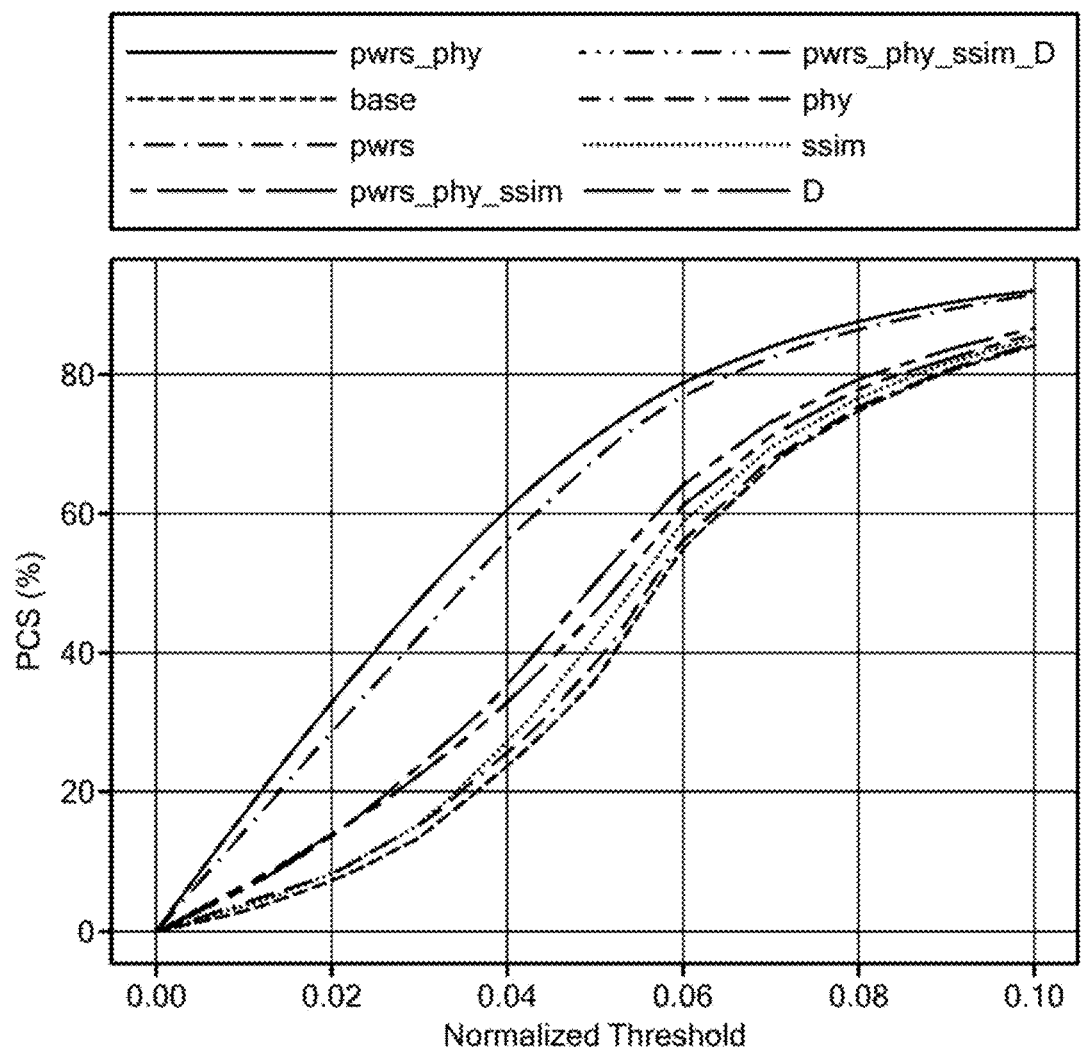
FIG. 5A illustrates $PCS_{cfs}$ plots for a PEye network ablation study with an input domain as RGB.
Figure 5B:
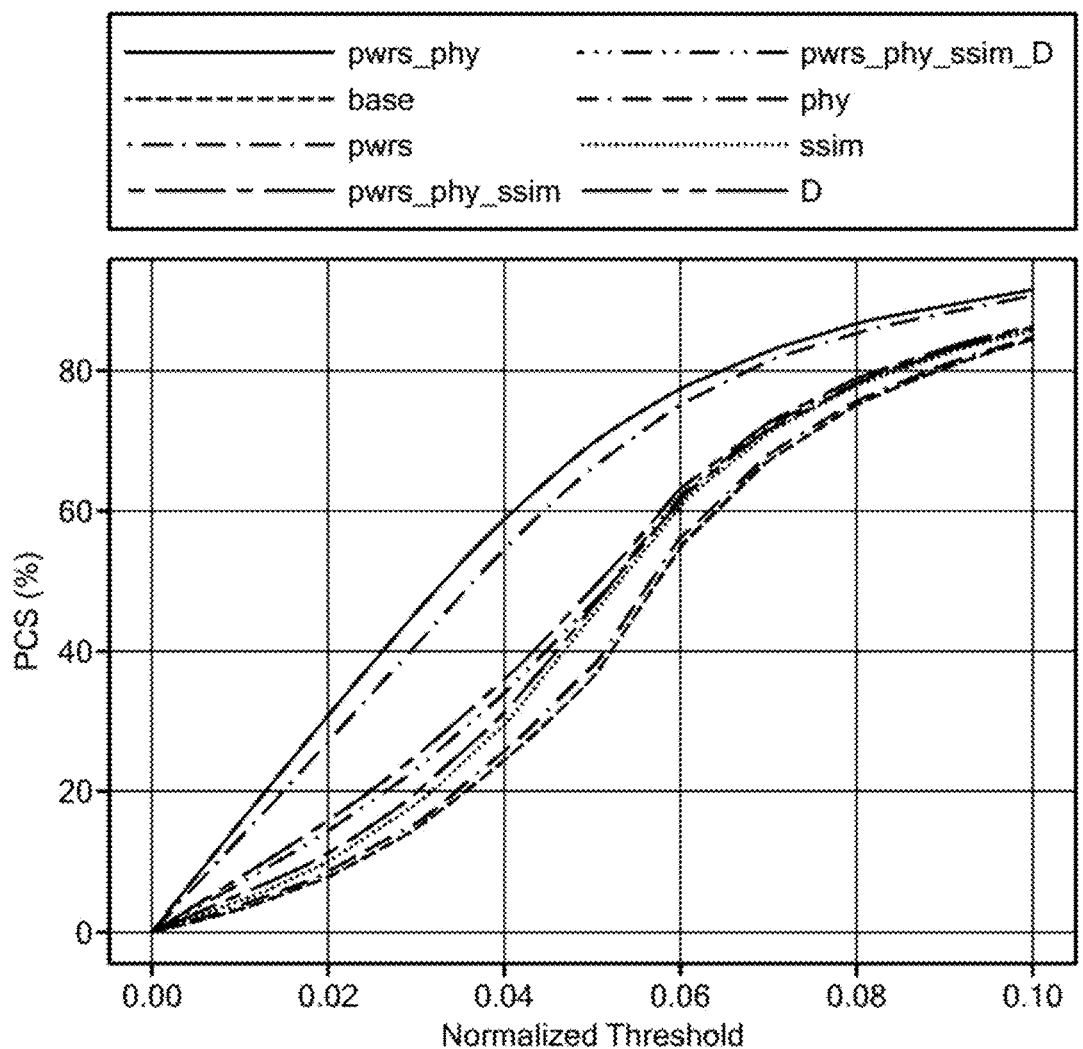
FIG. 5B illustrates $PCS_{cfs}$ plots for PEye network ablation study with input domain as LWIR.

Performance of tested configurations are given in Table 1 and Table 2 for RGB and LWIR input domains, respectively where base indicate the base model, pwrs, phy, ssim, D indicates the PEye network with inclusion of PWRS strategy, physical constraint, SSIM loss and discriminator loss with adversarial learning, respectively. The combination of approaches is concatenated with "-". The corresponding PCS plot is shown in FIG. 5. In both tables, it is apparent that although a typical $L_2$ regression strategy in the base model gives decent PSNR, but it shows worst performance for active area recovery as indicated by both $MSE_{efs}$ and $PCS_{efs}$ metrics. The PWRS supervision greatly enhanced the active area recovery. Introducing physics law constraint also enhanced the performance both individually or combined with the PWRS approach. There are also some other interesting findings in the ablation study: (i) MSE-only focused model (i.e. base) did not end up with best MSE/PSNR performance, and (ii) although not specially focused on active area, local structure regulation (SSIM and discriminator losses) or physical constraints both enhanced model performance in the active area. $L_2$ regression by itself can easily get stuck at local optimal by focusing only on average performance. Additional constraints however can push it out of the comfort zone towards optimum. Note that adding discriminator (D) loss or SSIM loss to the pwrs-phy though weakens regression oriented metrics such as $PCS_{efs}$ and $MSE_{efs}$, yet is in favor of the SSIM score and visual satisfaction. This may be due to the fact that $L_D$, $L_{ssim}$, and $L_{2\text{-}j}^{pwrs}$ all play a role for the active area pattern forming, which counter each other's effect. Yet, $L_{2\text{-}j}^{pwrs}$ is a sensing focused loss and is favored more by the regression oriented metrics.

Multi-Stage Setting

Figure 6:
FIG. 6 is an image of PM estimation outcomes of PEye network in pwrs-phy configuration with varying stages, with an RGB image as the input modality. The ground truth PM is on far left side followed by the PEye network results with 1-stage, 2-stage, and 3-stage configurations in accordance with various embodiments.

An analysis was also conducted to evaluate the effect of the multistage structure on model performance of pwrs-phy configuration, as shown in Table 3. The results demonstrate that additional stacked modules improved $PCS_{efs}$ metric slightly compared to the single stage configuration. However adding additional stages after 2 did not show notable improvements, as the major refinements were bound to happen in the early stages. A recovery example with different stages of PEye is also shown in FIG. 6, from which it can be seen with single stage structure, the recovery had more exaggerated and more pressure areas such as the torso area. With additional stages, the pattern became more slim and clean with higher SSIM and PSNR score.

TABLE 3

Performance of PEye network with different numbers of stages in pwrs-phy configuration with RGB or LWIR as input image modality.

| | $MSE_{efs}$(e-3) | PSNR | $PCS_{efs0.05}$ | $PCS_{efs0.1}$ | SSIM |
|---|---|---|---|---|---|
| RGB | | | | | |
| 1-Stage | 4.95 | 72.41 | 0.692 | 0.915 | 0.839 |
| 2-Stage | 4.78 | 73.12 | 0.722 | 0.918 | 0.894 |
| 3-Stage | 4.80 | 73.41 | 0.707 | 0.918 | 0.906 |
| LWIR | | | | | |
| 1-Stage | 4.82 | 69.44 | 0.689 | 0.910 | 0.834 |
| 2-Stage | 4.76 | 70.91 | 0.699 | 0.913 | 0.876 |
| 3-Stage | 4.81 | 71.50 | 0.695 | 0.912 | 0.887 |

Physical Parameters

The detail of the physical parameters of β is shown in Table 4.

TABLE 4

Physical parameters for PADS-PM listed in β. List of Physical Parameters in vector β

| weight (kg) | height (cm) | gender [0-1] | bust (cm) | waist (cm) |
|---|---|---|---|---|
| hip (cm) | upperArm-R (cm) | lowerArm-R (cm) | thigh-R (cm) | shank-R (cm) |

In the PEye approach, body weight is assumed to be the dominant factor for contact pressure generation. To further investigate the effect of other physical parameters for PM data reconstruction, participants' height, gender, and the anthropometric measurements of all of their major limbs (head, legs, and arms) and torso parts (bust, waist, and hip) were also measured, which are listed in Table 4. For gender, 0 is used for female and 1 for male. All limb measurements are from right side with the body symmetry assumption. These parameters are added gradually to theft in addition to the weight parameter, where the anthropometric measurements from 4th to 10th entries are added together. $PCS_{efs0.1}$ performance with varying length of are shown in FIGS. 7A-7D for both LWIR and RGB input modalities.

Figure 7A:
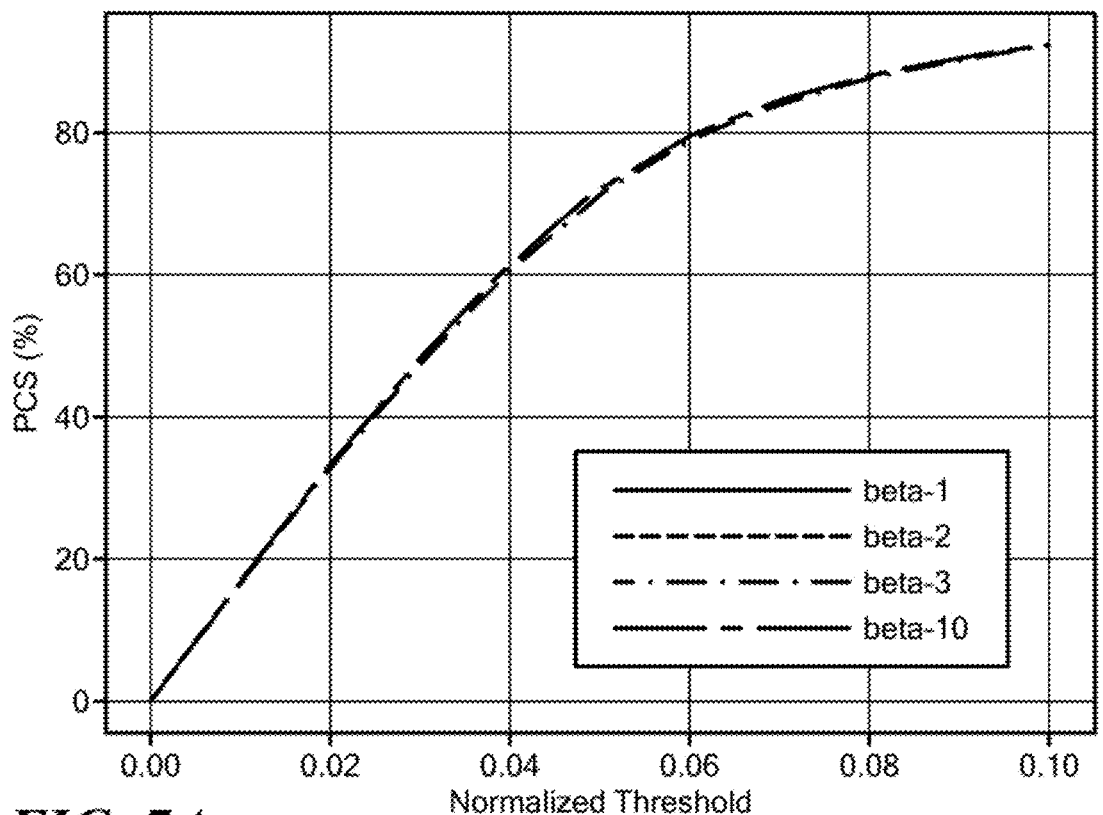
FIG. 7A illustrates performance of PEye network with pwrs-phy configuration with different physical vector β when input domain is RGB.
Figure 7B:
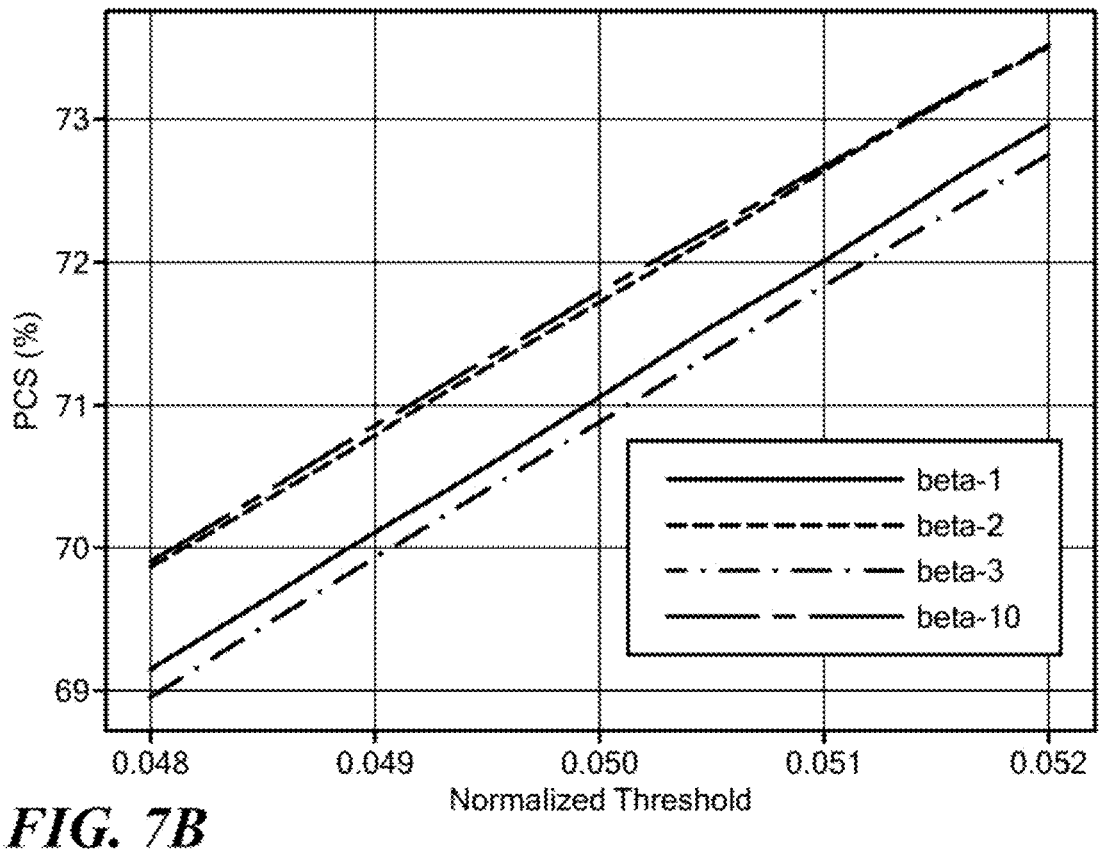
Figure 7C:
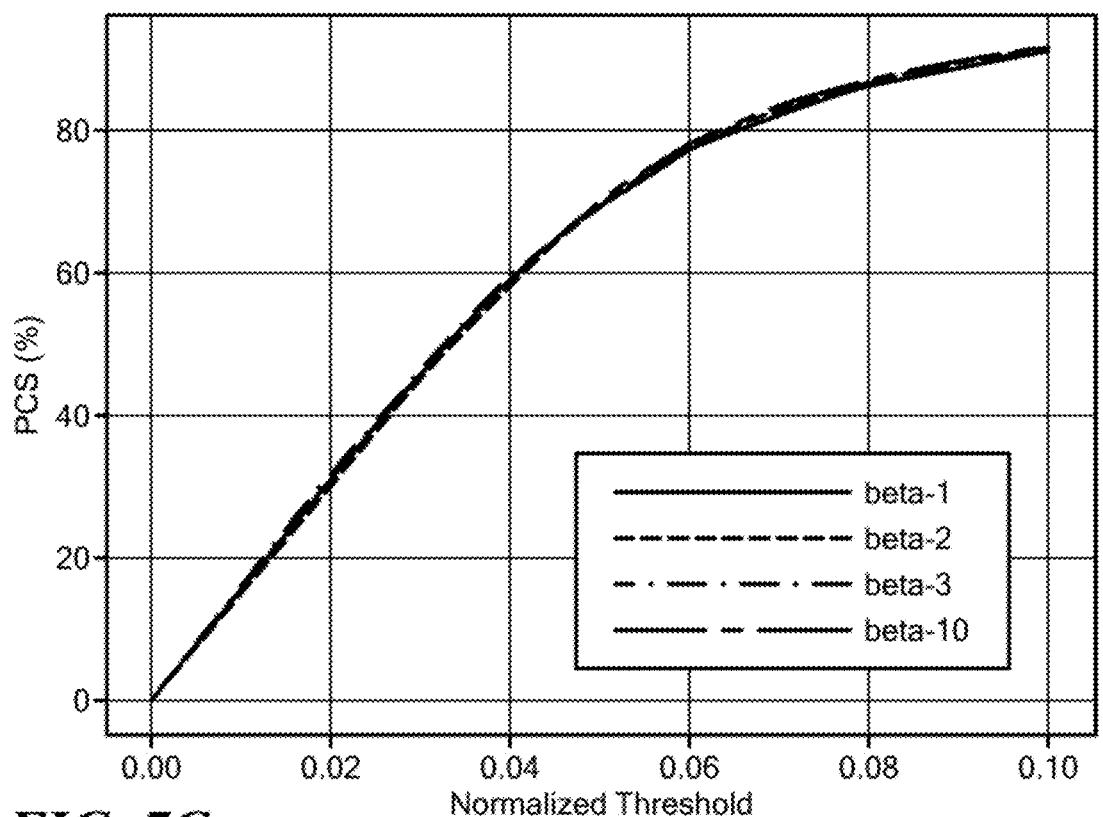
FIG. 7C illustrates performance of PEye network with pwrs-phy configuration with different physical vector β when input domain is LWIR.
Figure 7D:
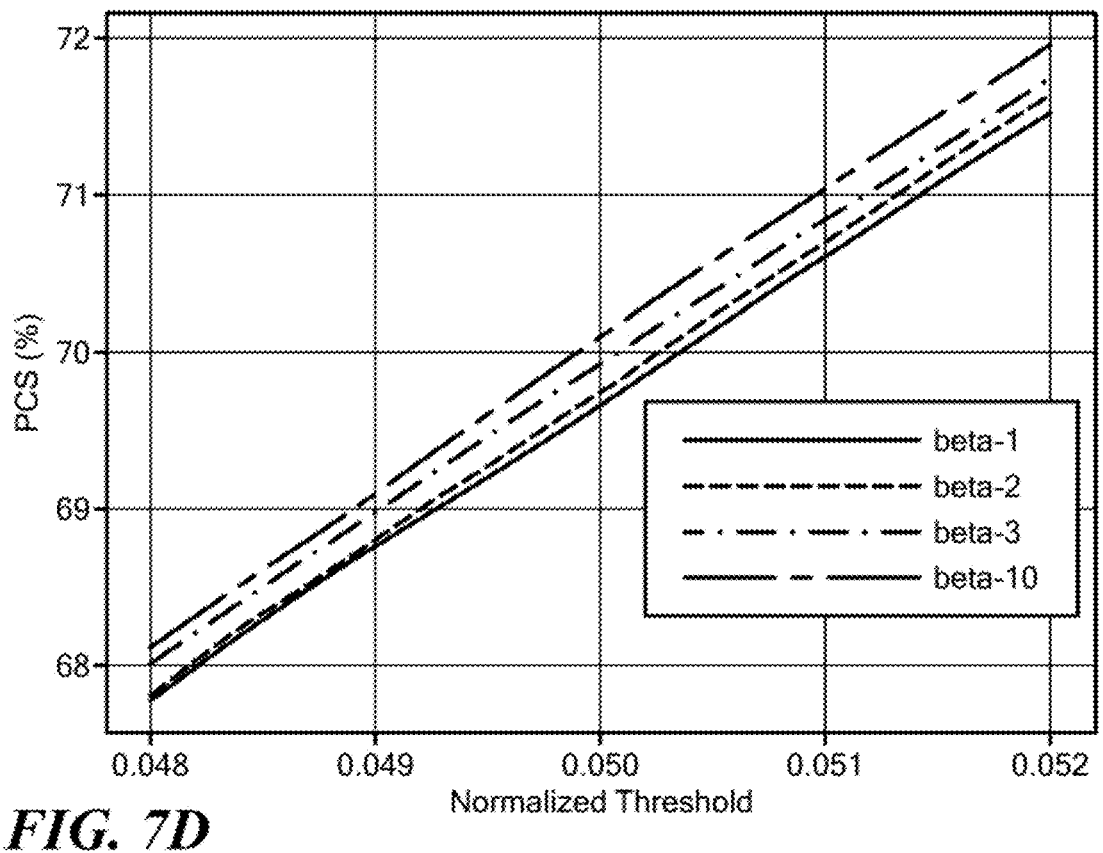

In order to illustrate the differences better, zoomed-in versions of both FIG. 7A and FIG. 7C are shown in FIG. 7B and FIG. 7D, respectively. Basically, additional physical inputs will improve the performance, but not always for a specific measure. For instance, while adding gender shows positive effect when LWIR is the input domain, that may not be the case when RGB images are used as the input. Full β version however gives the best performance in both domains. This is reasonable, as extended β provides more details of person's body shape and physiques, which are relevant factors in pressure map forming.

BMI Influence

Figure 8A:
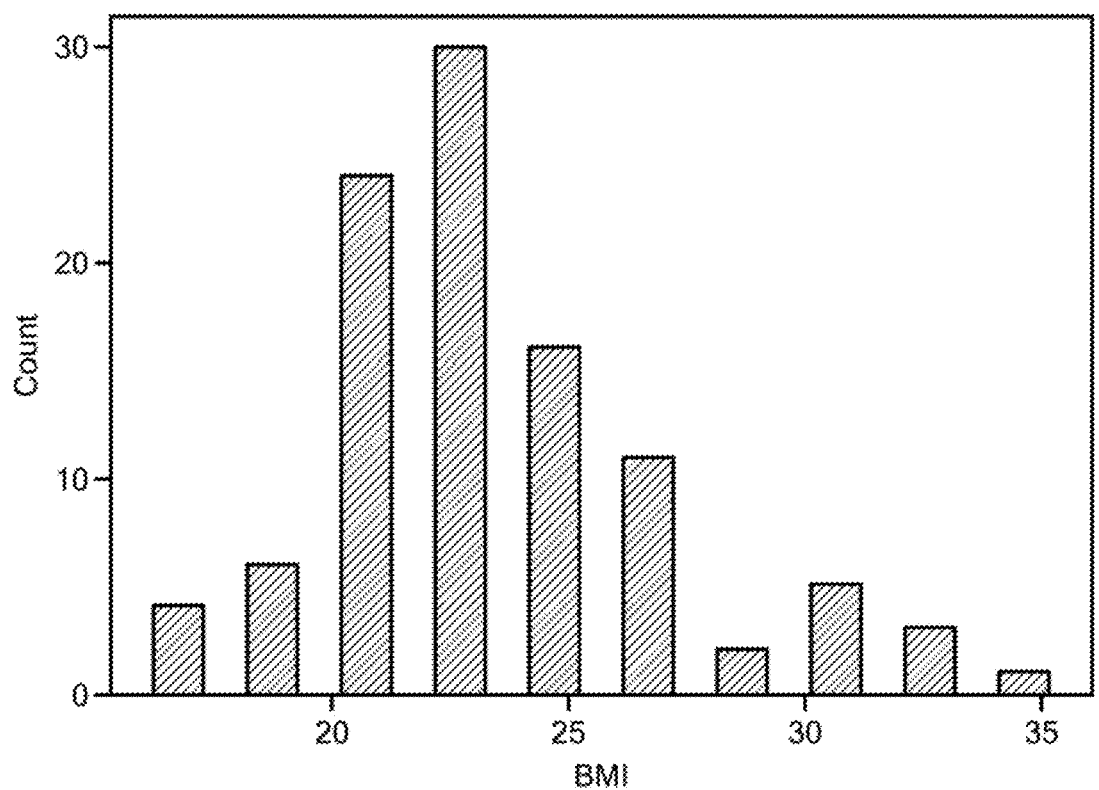
FIG. 8A illustrates the body mass index (BMI) of a whole SLP dataset.
Figure 8B:
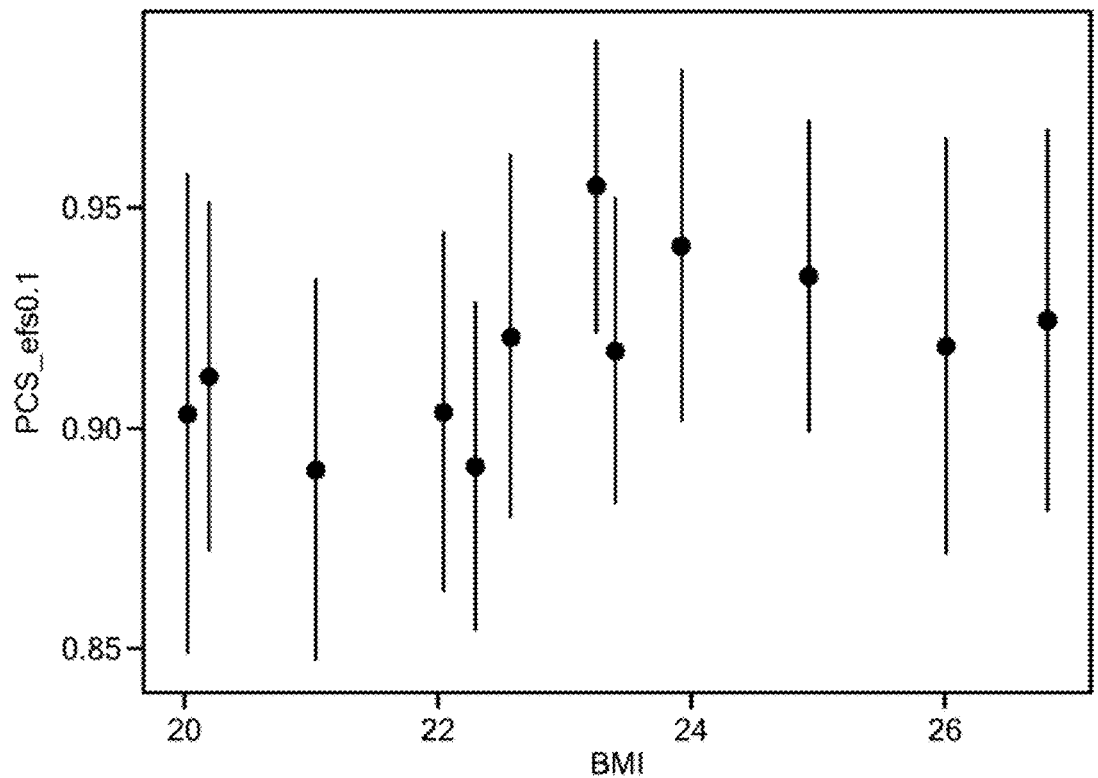
FIG. 8B illustrates body mass index (BMI) effect on PEye(pwrs-phy) performance for the SLP dataset of FIG. 8A, showing PCSefs0.1 performance against BMI with RGB as input, where the standard deviation (std) of each subject is employed for error plotting.
Figure 8C:
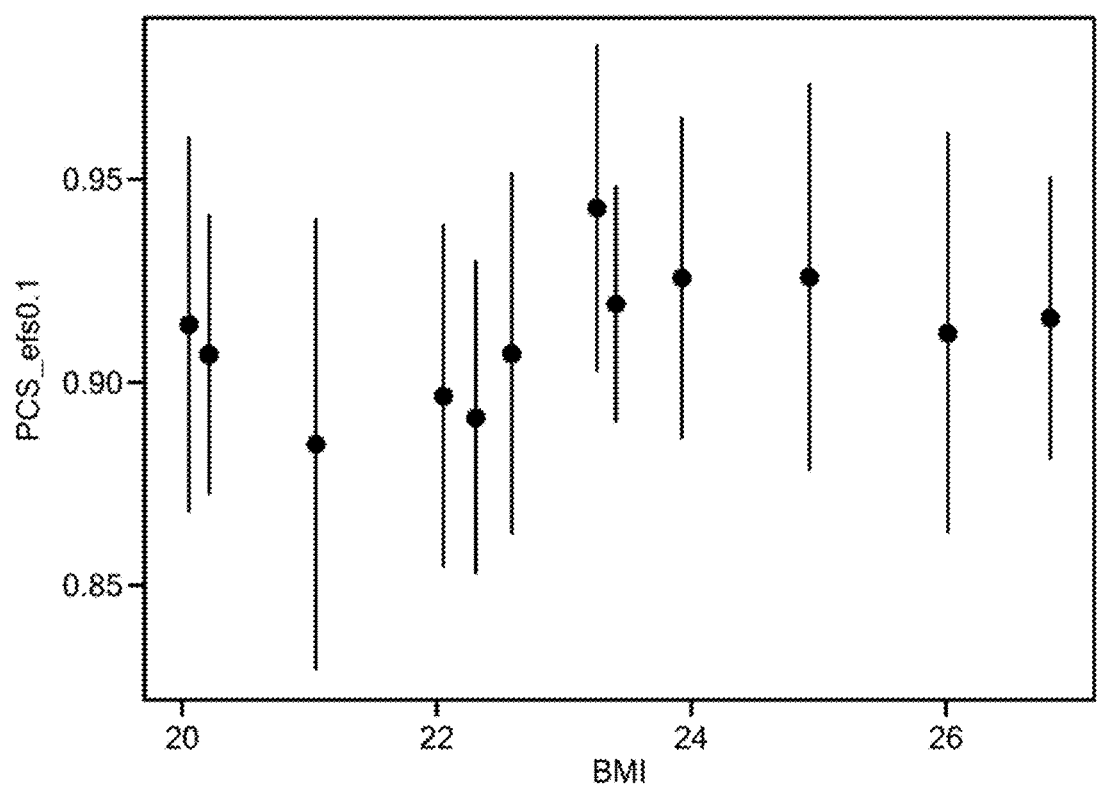
FIG. 8C illustrates body mass index (BMI) effect on PEye(pwrs-phy) performance for the SLP dataset of FIG. 8A, showing PCSefs0.1 performance against BMI with LWIR as input, where the standard deviation (std) of each subject is employed for error plotting.

Obesity contributes to immobility and subsequent pressure on skin surfaces. Prior studies have shown the correlation between the body mass index (BMI) and the pressure ulcer. Accordingly, here, the effects of BMI on PEye performance was studied. The BMI distribution of the dataset is shown in FIG. 8A. Here pwrs-phy configuration is employed which shows best $PCS_{efs0.1}$ in the ablation study. The $PCS_{efs0.1}$ performance of pressure estimation of each subject of the test set with varying BMI is shown in FIG. 8B and FIG. 8C for RGB and LWIR as input respectively, where the standard deviation (std) of each subject is employed as the error range. From the result, though not strictly linear, there is a slight increase trend of the $PCS_{efs0.1}$ performance with larger BMI. The best $PCS_{efs0.1}$ comes around BMI 24 but slightly drops when the BMI further goes higher.

Figure 9:
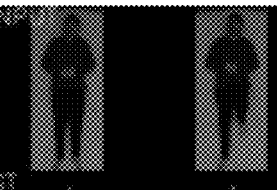
FIG. 9 illustrates qualitative results of PEye network ablation study with RGB and LWIR inputs, compared to the state-of-the-art.
Figure 10A:
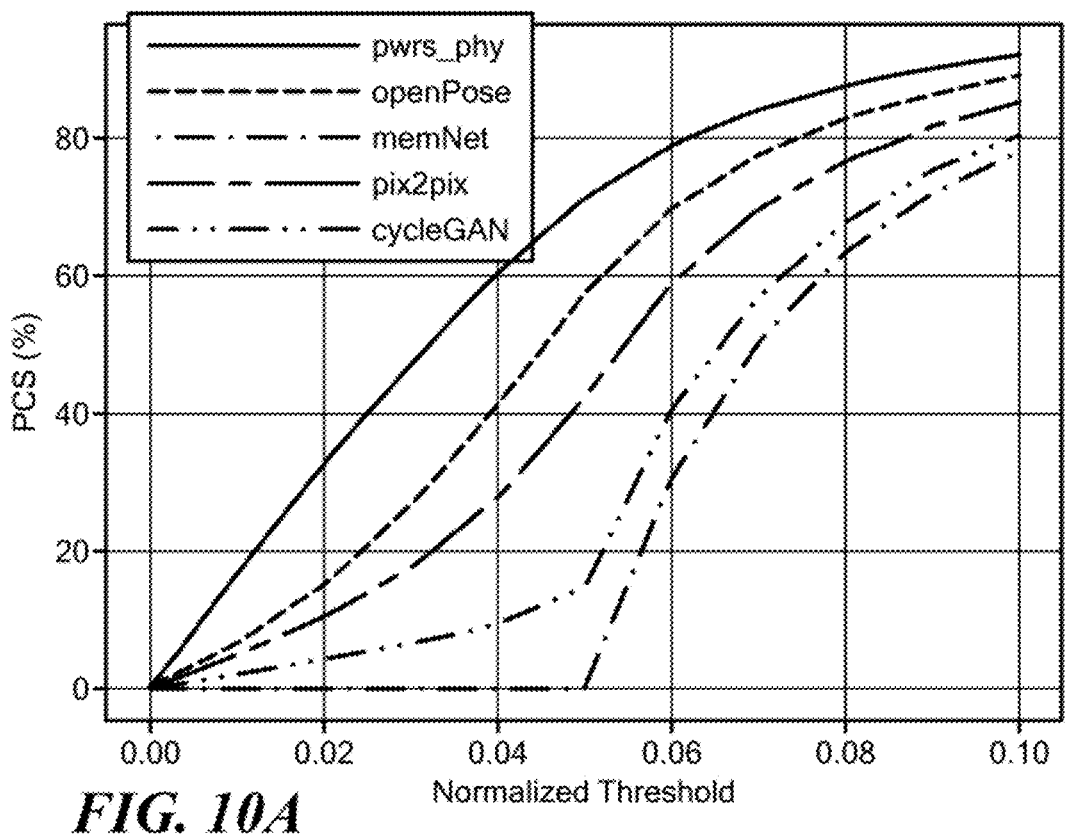
FIG. 10A illustrates $PCS_{cfs}$ plots comparing the PEye approach with the state-of-the-art with input domain as RGB.
Figure 10B:
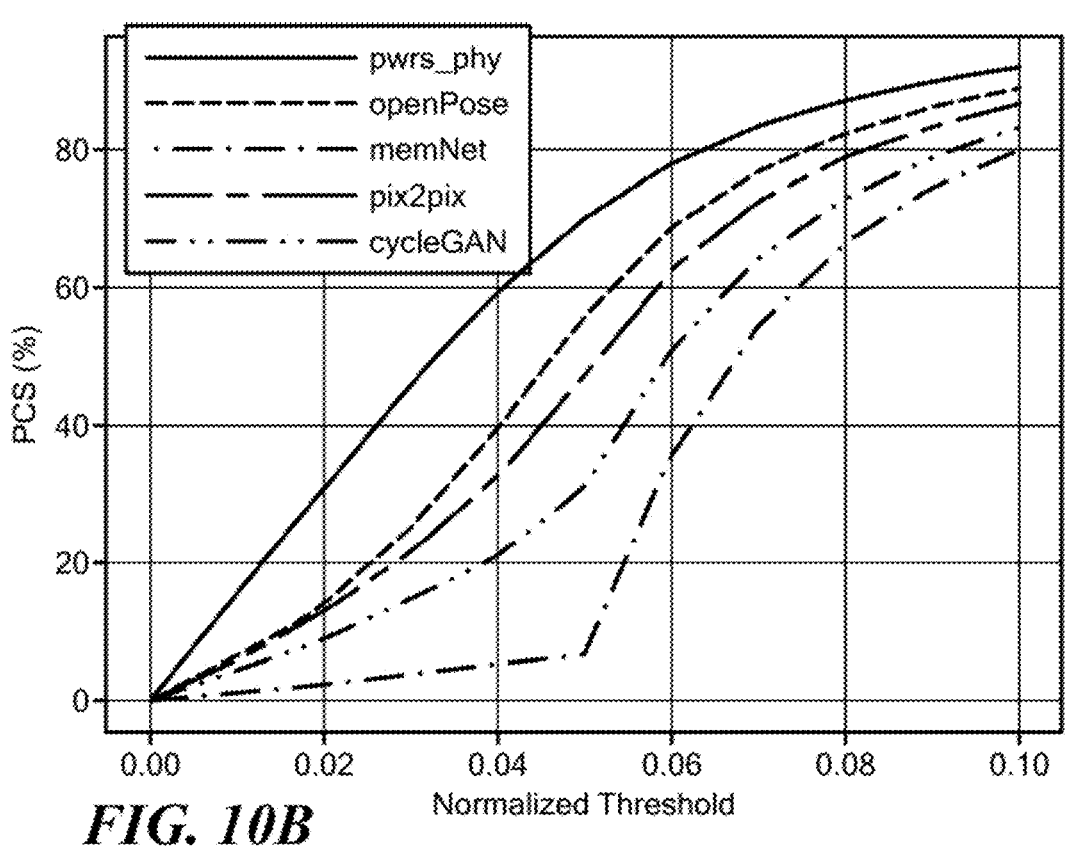
FIG. 10B illustrates $PCS_{cfs}$ plots comparing the PEye approach with the state-of-the-art with input domain as LWIR.
Figures 11A, 11B, 11C:
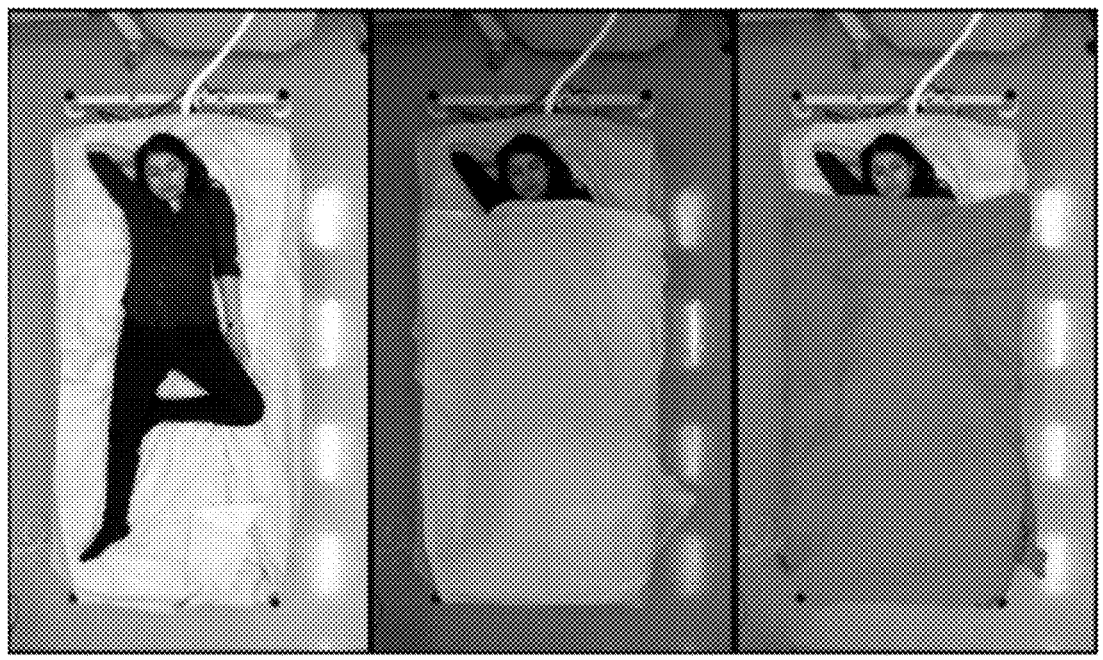
FIGS. 11A-F illustrate SLP image data samples from in-bed supine and side postures showing images captured using an RGB webcam. These images are taken from the participants without cover (FIGS. 11A, 11D), with a thin cover (FIGS. 11B, 11E), and with a thick cover (FIGS. 11C, 11F).
Figures 11D, 11E, 11F:
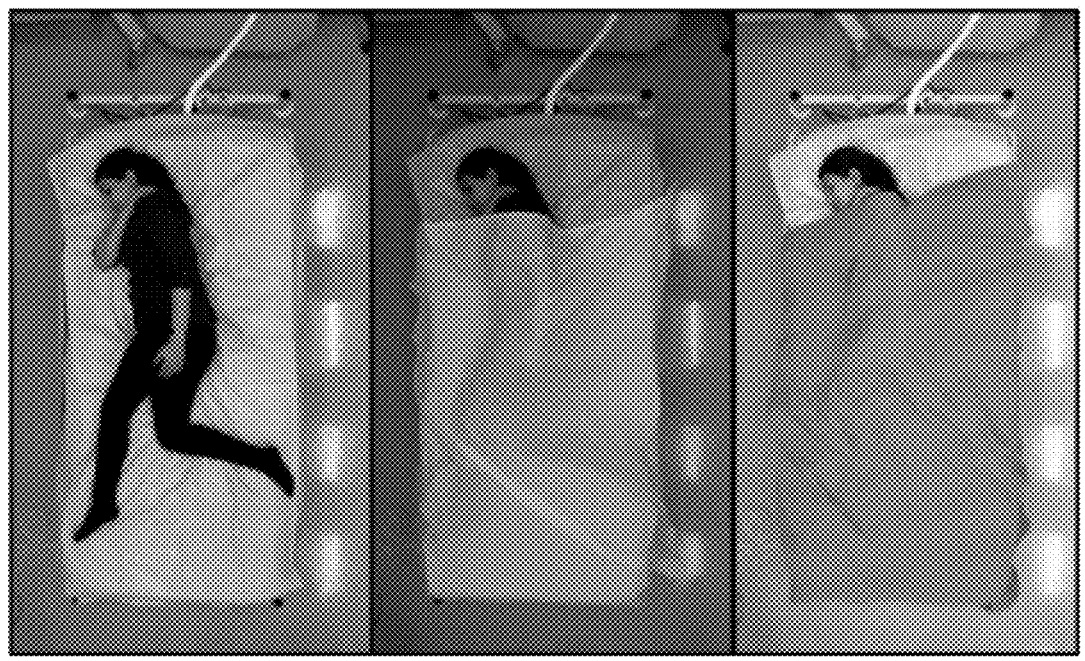

Qualitative comparison of the generated pressure maps from different PEye network configurations are also shown in FIG. 9. Due to the space constraints, only typical ablation configurations in the FIG. 9 are listed for qualitative comparison. The same sample pair from both RGB and LWIR domains was employed for an easier comparison across domains. In supine pose, base model was susceptible to ignoring pressure areas with small values such as arms, which were well-preserved in the pwrs-phy version. With additional SSIM and D supervision, the generated patterns were more visually pleasant. In a closer look, even the high frequency jitters effects of the raw measurements were well-preserved. However, overall estimated pressure was prone to be lower than ground truth. High pressure points were not always preserved, such as the peak areas around the elbows in the supine position and heel pressure area shrunk. These results once more reflect the different focus between the PM regression approach and the conventional image generation tasks. Image generation tasks usually focus on the generated patterns rather than the absolute regression accuracy, while in PEye, both patterns and the regression performance are important for an accurate sensing inference. Referring to the qualitative result in FIG. 9, it was also found that visually superior images usually held better effective PCS performance, which supports the feasibility of the PCS metric for this task.

Overall, PM reconstruction performance was similar in both RGB and LWIR domains and their metric performance were similar. Although LWIR loses much of the appearance details, yet the human body profile is still clearly preserved for semantic recognition of different body parts, which is required for contact pressure estimation.

Comparison with the State-of-the-Art

As the PEye dense PM regression task is described here for the first time, there are no other studies for an exact comparison. Instead, representative methods were chosen from similar tasks either for regression goal or the image translation goal. From the problem formulation perspective, as a dense regression problem, human pose estimation tasks can be selected as similar to that of PEye. From an image translation perspective, the present problem can also be described as generating maps in one domain using data in another domain. This task is also similar to the image translation task and can be conducted with or without pair-wise correspondence. So pix2pix and cycleGAN were chosen as representative models, respectively.

These models were adapted for the task with an "as it is" principle to minimize side effects of unnecessary changes. Open-Pose holds two branches of part affinity field (PAF) and joint confidence map (heat map). Since PAF is not available in the present case, only the confidence map branch with pressure map as its ground truth was kept for the supervision. Following its official implementation, the full resolution heat map was recovered via bilinear interpolation. As for memNet, it relies on residue learning mechanism which required identical data formats in input and output. The network was fed with gray scale image to match the single channel pressure map. Both pix2pix and cycleGAN adaptation were straightforward by replacing the input and output with the PEye data.

TABLE 5

Performance comparison of PEye network with pwrs-phy configuration with state-of-the art, with RGB as input image modality.

| Models | Metrics | | | | |
|---|---|---|---|---|---|
| | MSEefs(e−3) | PSNR | PCSefs0.05 | PCSefs0.1 | SSIM |
| pwrs-phy | 4.80 | 73.41 | 0.707 | 0.918 | 0.906 |
| openPose | 6.49 | 82.29 | 0.568 | 0.888 | 0.958 |
| memNet | 11.56 | 78.49 | 0.000 | 0.779 | 0.941 |
| pix2pix | 33.64 | 73.15 | 0.423 | 0.849 | 0.952 |
| cycleGAN | 42.28 | 71.49 | 0.148 | 0.803 | 0.951 |

TABLE 6

Performance comparison of PEye network with pwrs-phy configuration with state-of-the-art, with LWIR as input image modality.

| Models | Metrics | | | | |
|---|---|---|---|---|---|
| | MSEefs(e−3) | PSNR | PCSefs0.05 | PCSefs0.1 | SSIM |
| pwrs-phy | 4.81 | 71.50 | 0.695 | 0.912 | 0.887 |
| openPose | 6.98 | 82.10 | 0.551 | 0.881 | 0.957 |
| memNet | 10.92 | 36.08 | 0.067 | 0.795 | 0.089 |
| pix2pix | 8.07 | 78.74 | 0.469 | 0.858 | 0.950 |
| cycleGAN | 9.35 | 74.32 | 0.309 | 0.826 | 0.910 |

The comparison with the state-of-the-art is conducted in both RGB and LWIR domains as reported in Table 5 and Table 6, respectively. In $MSE_{efs}$ and $PCS_{efs}$ metric, pwrs-phy still showed noticeable improvements over other methods. OpenPose also showed a good performance especially in metrics such as PSNR and SSIM score. Referring to the qualitative results in FIG. 9, it can be seen that openPose presented a good overall pattern by localizing the high pressure areas most times correctly. However, these peaks were usually not high enough compared to the ground truth and the whole map ended up to be soft and blurry. Low pressure or small areas such as arm areas were also prone to be ignored. These results agree with the discussion earlier that human pose estimation focuses on confidence map as a byproduct for pose regression. Though effective to localize possible pressure concentration areas, yet it is not focusing on the regression accuracy but relative correctness.

MemNet basically failed to learn anything in the RGB domain and also performed poorly in LWIR domain. This may be due to the fact that image restoration was built on top of a quite similar input data from the same domain, where residue learning is reasonable. However, the task did not provide such near neighbor convenience. pix2pix provided nice details in local areas, yet overall it was prone to yield lower response than ground truth. Small parts such as foot and hand area were also sometimes missing in the recovery. CycleGAN only yielded partially recovery with distorted results. Point-wise supervision between correspondence is quite important for the regression purpose, which cycleGAN lacks. Cycle-GAN shows better recovery with LWIR input than RGB counterpart. This may be caused by the domain similarity between PM and LWIR, in which the body part areas highlighted by high temperature in LWIR correspond to high pressure areas in PM. It can also be seen that though high SSIM score is achieved by cycleGAN, the reconstruction is not necessarily satisfactory.

Practical Considerations

Generally, the experiments described herein were only conducted under a simulated application context which is still different from the real one for several reasons.

One example is that the patients in hospital are usually dressed in gowns which could results in occlusions and blurry in the RGB and LWIR respectively. To encourage the extensive participation from the community, the participants were not required to change to gowns for convenience. However, to address this, covered cases including a thin sheet and a thick blanket on the subject with the same pose for each of the modalities were collected for each frame as shown in FIGS. 11A-11L, which results in a similar occlusion and blurring effect. To study how these adverse conditions affect the PEye performance, the PEye (pwrs-phy) was retrained with mixed covered cases and its performance was tested with different cover conditions respectively as shown in Table 7. According to the results, PEye still shows a robust performance on those heavily occluded covered cases with only a slight performance drop in all reported metrics comparing to the no cover cases. We believe this is still reasonable. Our previous study shows that with proper supervision, existing SOTA pose models are capable to interpret the underlying human poses with the slight pattern clues over the cover. On the other hand, the contact pressure of lying human body highly depends on the given pose, body geometry and weight which are imported in the network with the proposed dual encoding structure. With this information provided, interpreting the underlying pressure is possible.

TABLE 7

Performance of PEye network with different numbers of stages in pwrs-phy configuration with RGB or LWIR as input image modality.

|  | $MSE_{efs}(e-3)$ | PSNR | $PCS_{efs0.05}$ | $PCS_{efs0.1}$ | SSIM |
|---|---|---|---|---|---|
| RGB |  |  |  |  |  |
| no cover | 5.13 | 75.13 | 0.695 | 0.913 | 0.918 |
| thin sheet | 5.50 | 73.94 | 0.660 | 0.905 | 0.905 |
| thick blanket | 6.08 | 73.53 | 0.616 | 0.895 | 0.892 |
| all | 5.57 | 74.20 | 0.657 | 0.904 | 0.905 |
| LWIR |  |  |  |  |  |
| no cover | 5.31 | 75.18 | 0.690 | 0.911 | 0.910 |
| thin sheet | 5.24 | 74.95 | 0.680 | 0.910 | 0.913 |
| thick blanket | 5.35 | 74.84 | 0.676 | 0.908 | 0.914 |
| all | 5.30 | 74.99 | 0.682 | 0.910 | 0.912 |

Figure 12A:
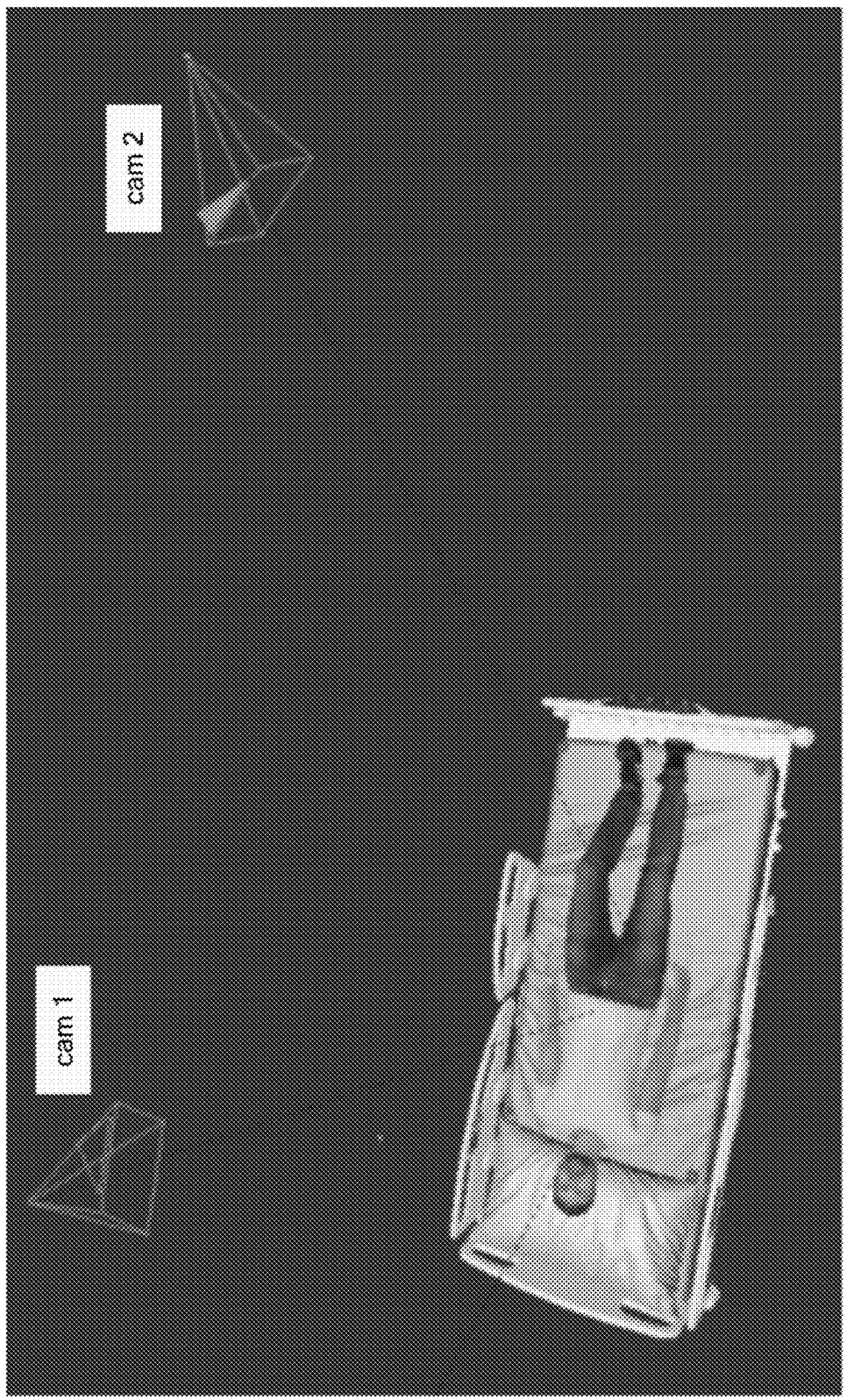
FIG. 12A illustrates homography mapping for an angled view (cam2) to a canonical view (cam1) for PEye monitoring, showing the canonical view and angled view setup.
Figure 12B:
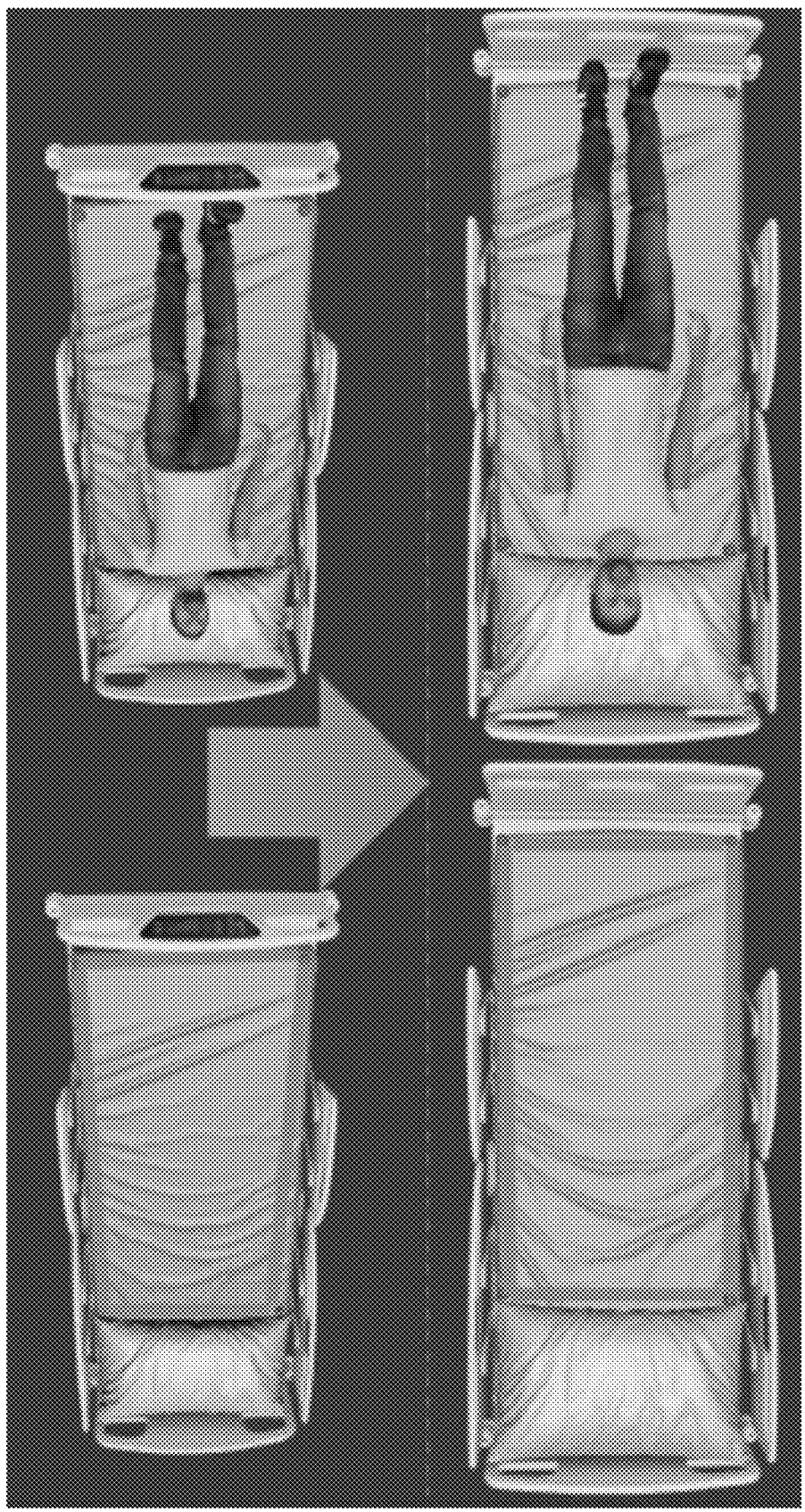
FIG. 12B illustrates homography mapping for the angled view (cam2) to the canonical view (cam1) for PEye monitoring, showing homography mapping from the mattress corner points to a target bounding box. As shown, overlaid corner dots stand for the bed corner points and an overlaid box extending around a perimeter of an exposed portion of the mattress stands for a homography mapping area from angled view to the canonical bounding box.

In practical application, the results indicate installation of the camera(s) directly above the bed for best effect. However, if the camera can not be installed in a canonical way but with slight angle, a homography mapping can be employed to map the angled view-point back to a canonical view with corresponding points from a reference plan as shown in FIGS. 12A and 12B. Because the camera is substantially fixed after installation and the bed surface comes with a rectangular shape which can be directly mapped to a target bounding box in an image, this calibration can be conducted at the beginning of a new session.

Integration with Pose Estimation Systems

In some embodiments, the PEye system 100 can be used in connection with one or more 2-dimensional (2D) or 3-dimensional (3D) pose estimation systems for obtaining additional training data and for improving the accuracy of pose information used in connection with the contact pressure estimation methods via contactless imaging. Such pose estimation systems can include, for example, but not limited to, substantially 2D systems such as those depicted and described in U.S. Pat. No. 11,222,437, which is hereby incorporated herein in its entirety, or substantially 3D systems such as those depicted and described in U.S. patent application Ser. No. 17/403,933, which is also hereby incorporated herein in its entirety.

It will be apparent in view of this disclosure that, in some embodiments, the PEye system 100 and the pose estimation system can include similar components (e.g., computing device 101 having a processor 103 and memory 105, imaging devices 107 configured for RGB and/or LWIR, surface 115 on which subject 111 is placed, physical parameter sensor 113). In some embodiments, additional components may also be used in connection with the pose estimation system such as, for example, a cooling mat atop the surface but under the subject for improving thermal contrast for LWIR imaging.

Treatment Scenarios

Integration with Posture Scheduling Systems

In some embodiments, the PEye system alone and/or the PEye system as integrated with the pose estimations systems can be integrated with a posture scheduling system to provide one or more posture schedules for use by one or more nurses or other medical professionals responsible for preventing pressure ulcers in each subject (patient). Posture scheduling systems can include, for example, those depicted and described in Ostadabbas, S.; Yousefi, R.; Faezipour, M.; Tamil, L.; and Pompeo, M. 2011. A Posture Scheduling Algorithm Using Constrained Shortest Path to Prevent Ulcers. 2011 *IEEE International Conference on Bioinformatics and Biomedicine* 327-332, which is hereby incorporated herein in its entirety or those depicted and described in Ostadabbas, S.; Yousefi, R.; Nourani, M.; Faezipour, M.; Tamil, L.; and Pompeo, M. 2012. A Resource-Efficient Planning for Pressure Ulcer Prevention. *IEEE Transactions on Information Technology in Biomedicine*, Vol. 16, No. 6, November 2012 1265-1273, which is also incorporated herein in its entirety.

Figure 13:
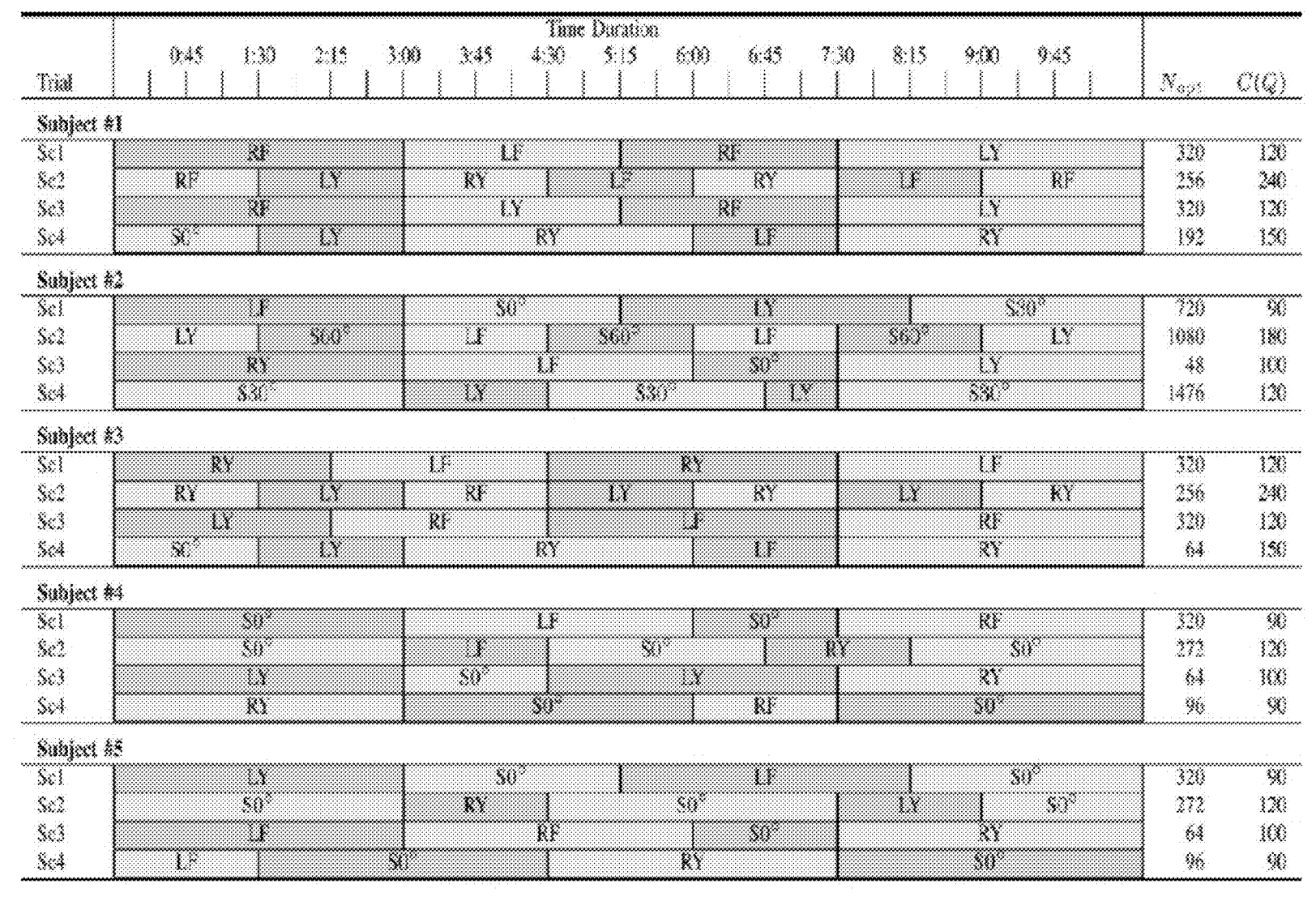

Such posture scheduling systems generally consider the factors of patient condition and the total amount of nursing effort required to execute the schedule to develop a selection of one or more optimized schedules for reposturing a particular patient. For example, as shown in FIG. 13 and described in Ostadabbas et al. (2012), posture scheduling can be generated on a per-subject basis and for different patient condition scenarios.

In the master schedule of FIG. 13, seven different common postures are modeled including Supine (S0°, S30°, S60°), Right Yearner (RY), Right Foetus (RF), Left Yearner (LY), and Left Foetus (LF) wherein the difference between the three Supine postures is the angle of inclination of the bed. The treatment scenarios studied include Sc1: All of the body areas are healthy without any symptom of ulceration, Sc2: Reddened skin on the right and left buttocks, Sc3: Reddened skin on the central sacrum area, and Sc4: Reddened skin on the left ankle and left back. Nopt indicates the number of optimal solutions (i.e., the number of solutions providing a desired patient outcome in a minimum amount of nursing effort C(Q).

Within the context of contact pressure estimation via contactless imaging, such contact pressure data can replace and/or supplement the burdensome and error-prone task of manually assessing each patient for a red skin tone (at which time ulceration has already begun) to further reduce nursing effort while simultaneously improving patient outcomes. Still further, in some embodiments, to the extent a transition between one or more Supine postures is desirable, the system of the subject patent application can be configured to automatically control the bed to increase or decrease the incline thereof, obviating the need for nurse intervention during that particular repositioning cycle.

CONCLUSION

The technology described herein provides methods and system for recovering the contact pressure between a lying human and the bed surface from a vision signal (RGB or LWIR) in a dense regression manner. The PEye approach can lead to a cost-efficient high resolution pressure mapping, since expensive pressure map signals can be recovered from low cost vision signals. A large-scale in-bed pose dataset was also formed that contains simultaneously collected multi-domain data from human while lying in bed, with large enough size to train deep neural networks from scratch. Evaluations of the PEye approach were conducted with RGB and LWIR as source domains and its performance compared extensively across similar tasks with their state-of-the-art models. From the comparison, it was also found that although formulated exactly the same way, every task holds its specific context and focus, in which a well-performed model for one task does not necessarily guarantee optimal performance in another task. In the evaluation, it was noticed that when using the PEye approach some failure cases with fake pressure in unsupported areas may appear. This usually happens when body parts are partially supported by each other and not the bed and the network fails to recognize such elevation and reports false pressures.

REFERENCES

Andriluka, M.; Pishchulin, L.; Gehler, P.; and Schiele, B. 2014. 2d human pose estimation: New benchmark and state of the art analysis. In *Proceedings of the IEEE Conference on computer Vision and Pattern Recognition*, 3686-3693.

Batista, G. E.; Prati, R. C.; and Monard, M. C. 2004. A study of the behavior of several methods for balancing machine learning training data. *ACM SIGKDD explorations newsletter* 6(1): 20-29.

Bishop, C. M. 2006. *Pattern recognition and machine learning.* springer.

Black, J.; Baharestani, M. M.; Cuddigan, J.; Dorner, B.; Eds-berg, L.; Langemo, D.; Posthauer, M. E.; Ratliff, C.; Taler, G.; et al. 2007. National Pressure Ulcer Advisory Panel's updated pressure ulcer staging system. *Advances in skin & wound care* 20(5): 269-274.

Brock, A.; Donahue, J.; and Simonyan, K. 2018. Large scale gan training for high fidelity natural image synthesis. *arXiv preprint arXiv:* 1809.11096.

Cao, Z.; Hidalgo, G.; Simon, T.; Wei, S.-E.; and Sheikh, Y. 2018. OpenPose: realtime multi-person 2D pose estimation using Part Affinity Fields. In *arXiv preprint arXiv:* 1812.08008.

Chawla, N. V.; Bowyer, K. W.; Hall, L. O.; and Kegelmeyer, W. P. 2002. SMOTE: synthetic minority over-sampling technique. *Journal of artificial intelligence research* 16: 321-357.

Clever, H. M.; Kapusta, A.; Park, D.; Erickson, Z.; Chitalia, Y.; and Kemp, C. C. 2018. 3d human pose estimation on a configurable bed from a pressure image. In 2018 *IEEE/RSJ International Conference on Intelligent Robots and Systems (IROS)*, 54-61. IEEE.

Greminger, M. A.; and Nelson, B. J. 2004. Vision-based force measurement. *IEEE Transactions on Pattern Analysis and Machine Intelligence* 26(3): 290-298.

Hartley, R.; and Zisserman, A. 2003. *Multiple view geometry in computer vision.* Cambridge university press.

Herland, M.; Khoshgoftaar, T. M.; and Bauder, R. A. 2018. Big data fraud detection using multiple Medicare data sources. *Journal of Big Data* 5(1): 29.

Isola, P.; Zhu, J.-Y.; Zhou, T.; and Efros, A. A. 2017. Image-to-image translation with conditional adversarial networks. In *Proceedings of the IEEE conference on computer vision and pattern recognition,* 1125-1134.

Japkowicz, N. 2000. The class imbalance problem: Significance and strategies. In *Proc. of the Int'l Conf. on Artificial Intelligence, volume* 56. Citeseer.

Johnson, J. M.; and Khoshgoftaar, T. M. 2019. Survey on deep learning with class imbalance. *Journal of Big Data* 6(1): 27.

Kingma, D. P.; and Ba, J. 2014. Adam: A method for stochastic optimization. *arXiv preprint arXiv:* 1412.6980.

Kubat, M.; Matwin, S.; et al. 1997. Addressing the curse of imbalanced training sets: one-sided selection. In *Icml, volume* 97,179-186. Citeseer.

Ledig, C.; Theis, L.; Huszár, F.; Caballero, J.; Cunningham, A.; Acosta, A.; Aitken, A.; Tejani, A.; Totz, J.; Wang, Z.; et al. 2017. Photo-realistic single image super-resolution using a generative adversarial network. In *Proceedings of the IEEE conference on computer vision and pattern recognition,* 4681-4690.

Liu, S.; Yin, Y.; and Ostadabbas, S. 2019. In-bed pose estimation: Deep learning with shallow dataset. *IEEE journal of translational engineering in health and medicine* 7: 1-12.

Long, J.; Shelhamer, E.; and Darrell, T. 2015. Fully convolutional networks for semantic segmentation. *Proceedings of the IEEE conference on Computer Vision and Pattern Recognition* 3431-3440.

Martinez, M.; Rybok, L.; and Stiefelhagen, R. 2015. Action recognition in bed using BAMs for assisted living and elderly care. In 2015 *14th IAPR International Conference on Machine Vision Applications (MVA),* 329-332. IEEE.

Murthy, J. N.; Van Jaarsveld, J.; Fei, J.; Pavlidis, I.; Harrykissoon, R. I.; Lucke, J. F.; Faiz, S.; and Castriotta, R. J. 2009. Thermal infrared imaging: a novel method to monitor airflow during polysomnography. *Sleep* 32(11): 1521-1527.

Newell, A.; Yang, K.; and Deng, J. 2016. Stacked hourglass networks for human pose estimation. *European Conference on Computer Vision* 483-499.

Nguyen, A. V.; Cohen, N. J.; Lipman, H.; Brown, C. M.; Molinari, N.-A.; Jackson, W. L.; Kirking, H.; Szymanowski, P.; Wilson, T. W.; Salhi, B. A.; et al. 2010. Comparison of 3 infrared thermal detection systems and self-report for mass fever screening. *Emerging infectious diseases* 16(11): 1710.

Ostadabbas, S.; Sebkhi, N.; Zhang, M.; Rahim, S.; Anderson, L. J.; Lee, F. E.-H.; and Ghovanloo, M. 2015. A vision-based respiration monitoring system for passive airway resistance estimation. *IEEE Transactions on biomedical engineering* 63(9): 1904-1913.

Ostadabbas, S.; Yousefi, R.; Faezipour, M.; Nourani, M.; and Pompeo, M. 2011. Pressure ulcer prevention: An efficient turning schedule for bed-bound patients. *Life Science Systems and Applications Workshop (LiSSA), 2011 IEEE/ NIH* 159-162.

Pham, T.-H.; Kheddar, A.; Qammaz, A.; and Argyros, A. A. 2015. Towards force sensing from vision: Observing hand-object interactions to infer manipulation forces. In *Proceedings of the IEEE conference on computer vision and pattern recognition,* 2810-2819.

Poh, M.-Z.; McDuff, D. J.; and Picard, R. W. 2010. Advancements in noncontact, multiparameter physiological measurements using a webcam. *IEEE transactions on biomedical engineering* 58(1): 7-11.

Rao, R. B.; Krishnan, S.; and Niculescu, R. S. 2006. Data mining for improved cardiac care. *ACM SIGKDD Explorations Newsletter* 8(1): 3-10.

Salimans, T.; Goodfellow, I.; Zaremba, W.; Cheung, V.; Radford, A.; and Chen, X. 2016. Improved techniques for training gans. In *Advances in neural information processing systems,* 2234-2242.

Sun, K.; Xiao, B.; Liu, D.; and Wang, J. 2019. Deep High-Resolution Representation Learning for Human Pose Estimation. In *CVPR.*

Tai, Y.; Yang, J.; Liu, X.; and Xu, C. 2017. Memnet: A persistent memory network for image restoration. In *Proceedings of the IEEE international conference on computer vision,* 4539-4547.

Velardo, C.; and Dugelay, J.-L. 2010. Weight estimation from visual body appearance. In *2010 Fourth IEEE International Conference on Biometrics: Theory, Applications and Systems (BTAS),* 1-6. IEEE.

Wang, Z.; Bovik, A. C.; Sheikh, H. R.; Simoncelli, E. P.; et al. 2004. Image quality assessment: from error visibility to structural similarity. *IEEE transactions on image processing* 13(4): 600-612.

Wei, S.-E.; Ramakrishna, V.; Kanade, T.; and Sheikh, Y. 2016. Convolutional pose machines. *Proceedings of the IEEE Conference on Computer Vision and Pattern Recognition* 4724-4732.

Wei, W.; Li, J.; Cao, L.; Ou, Y.; and Chen, J. 2013. Effective detection of sophisticated online banking fraud on extremely imbalanced data. *World Wide Web* 16(4): 449-475.

Yin, Z.; and Shi, J. 2018. Geonet: Unsupervised learning of dense depth, optical flow and camera pose. In *Proceedings of the IEEE Conference on Computer Vision and Pattern Recognition,* 1983-1992.

Zhang, Y.; Tian, Y.; Kong, Y.; Zhong, B.; and Fu, Y. 2018. Residual dense network for image super-resolution. In *Proceedings of the IEEE Conference on Computer Vision and Pattern Recognition,* 2472-2481.

Zhu, J.-Y.; Park, T.; Isola, P.; and Efros, A. A. 2017. Unpaired image-to-image translation using cycle-consistent adversarial networks. In *Proceedings of the IEEE international conference on computer vision,* 2223-2232.

As used herein, "consisting essentially of" allows the inclusion of materials or steps that do not materially affect the basic and novel characteristics of the claim. Any recitation herein of the term "comprising," particularly in a description of components of a composition or in a description of elements of a device, can be exchanged with "consisting essentially of" or "consisting of."

The present technology has been described in conjunction with certain preferred embodiments and aspects. It is to be understood that the technology is not limited to the exact details of construction, operation, exact materials or embodiments or aspects shown and described, and that various modifications, substitution of equivalents, alterations to the compositions, and other changes to the embodiments and aspects disclosed herein will be apparent to one of skill in the art.

What is claimed is:

1. A system for generating a contact pressure map of a human subject lying on a surface, comprising:
   one or more imaging devices oriented toward the surface, the imaging devices comprising one or more imaging sensors capable of generating red-green-blue (RGB) images, long wavelength infrared (LWIR) images, or depth images; and
   a processor and memory, including a trained model for generating the contact pressure map, the trained model trained with a dataset of human subjects in lying poses comprising physical parameters of the human subjects, a plurality of pressure maps, and corresponding plurality of images of the human subjects in lying poses, the plurality of images comprising images generated from at least one imaging modality, including an RGB imaging modality, an LWIR imaging modality, or a depth imaging modality;
   wherein the processor is in communication with the one or more imaging devices to receive one or more images of the human subject lying on the surface, the images of the human subject comprising RGB images, LWIR images, or depth images, and a source to receive physical data representing one or more physical parameters of the human subject lying on the surface; and
   wherein the processor and memory is operative to generate, using the trained model, a pressure map of the human subject lying on the surface based on the one or more images of the human subject lying on the surface and the one or more physical parameters of the human subject lying on the surface.

2. The system of claim 1, wherein the processor is operative to encode signals representing the images of the human subject lying on the surface and the physical data representing the physical parameters of the human subject lying on the surface separately, concatenate the encoded signals, and decode the signals jointly.

3. The system of claim 1, wherein the dataset further comprises one or more physical parameters corresponding to a human subject of each image.

4. The system of claim 1, wherein the source of the one or more physical parameters is at least one of a memory storing patient information, a scale positioned on or integrated into the surface, or an image processing module.

5. The system of claim 1, wherein the one or more imaging devices includes at least one of a camera, a video camera, an infrared camera, an infrared video camera, a depth camera, a CCD sensor, a CMOS sensor, an infrared sensor, a depth sensor, a structural light sensor, a time of flight sensor, a camera array, a LIDAR scanner, a 3D camera, or combinations thereof.

6. The system of claim 1, wherein the surface is at least one of a hospital bed, a residential bed, a surgical table, a cot, a gurney, a floor of a kennel or crate for animal use, or a crib or bassinet.

7. A method for generating a contact pressure map of a human subject lying on a surface comprising:
   providing a processor and memory, including a trained model for generating the contact pressure map, the trained model trained with a dataset of human subjects in lying poses comprising physical parameters of the human subjects, a plurality of pressure maps, and corresponding plurality of images of the human subjects in lying poses, the plurality of images comprising images generated from at least one imaging modality, including a red-green-blue (RGB) imaging modality, a long wavelength infrared (LWIR) imaging modality, or a depth imaging modality;

receiving, at the processor, one or more images of the human subject lying on the surface from one or more imaging devices oriented toward the surface, the imaging devices comprising one or more imaging sensors and the images of the human subject comprising RGB images, LWIR images, or depth images;

receiving, at the processor, physical data representing one or more physical parameters of the human subject lying on the surface from a physical parameter source; and generating, using the trained model, the contact pressure map of the human subject lying on the surface based on the one or more images of the human subject lying on the surface and the one or more physical parameters of the human subject lying on the surface.

8. The method of claim 7, wherein the processor is operative to encode signals representing the images of the human lying on the surface and the physical data representing the one or more physical parameters of the human lying on the surface separately, concatenate the encoded signals, and decode the signals jointly.

9. The method of claim 7, further comprising generating the dataset of the plurality of human lying poses by gathering images of human lying poses according to at least one imaging modality, including at least one of the red-green-blue (RGB) imaging modality, the long wavelength infrared (LWIR) imaging modality, and the depth imaging modality.

10. The method of claim 9, further comprising:
labeling the poses; and
storing the gathered images as labeled poses in a database.

11. The method of claim 10, further comprising training a model for generating a contact pressure map of a human lying on a surface with the dataset.

12. The method of claim 11, wherein the model can be expressed as:

$$L^{total} = \lambda_{pwrs} L_{2-1}^{pwrs} + \lambda_{phy} L_2^{phy};$$

wherein $$L_{2-1}^{pwrs} = \lambda_{L_2} \sum_{i=0}^{M} \sum_{j=0}^{N} (\hat{y}(i,j) - y(i,j))^2 (1/p(y(i,j) + \xi));$$

wherein $$L_2^{phy} = \left( c \sum_i \sum_j \hat{y}(i,j) - w_b \right)^2;$$

wherein $L_{2-1}^{pwrs}$ is a pixel-wise resampling (PWRS) loss;
wherein $L_2^{phy}$ is a physical loss;
wherein $\lambda_{pwrs}$ and $\lambda_{phy}$ stand for weights applied to each loss term, respectively;
wherein y(i, j) represents a pixel value at i and j coordinates of a pressure map;
wherein p(y(i, j)+ξ) is a density function of y and ξ is a hallucinated weight;
wherein M is a row size of the pressure map;
wherein N is a column size of the pressure map;
wherein $w_b$ stands for human body weight; and
wherein c is a contact area with a bed represented by each pixel of the pressure map.

13. The method of claim 10, further comprising correlating one or more physical parameters corresponding to a human subject of each of the gathered images to a corresponding one of the labeled poses in the database.

14. The method of claim 7, wherein the physical parameters include one or more of weight, height, gender, bust, waist, hip, upper arm circumference, lower arm circumference, thigh circumference, and shank circumference.

15. The method of claim 7, wherein the dataset further comprises one or more physical parameters corresponding to a human subject of each image of each set of images.

16. The method of claim 7, further comprising transmitting instructions to a medical professional device for repositioning a patient to a different posture.

17. The method of claim 16, wherein the different posture is determined according to a posture scheduling algorithm.

18. The method of claim 7, wherein the surface is a repositionable bed and the method further comprises transmitting instructions to the repositionable bed for repositioning a patient to a different posture.

19. A method for generating a contact pressure map of a human subject lying on a surface, comprising:
generating a dataset of a plurality of human subjects in lying poses, comprising gathering physical parameters of the human subjects, a plurality of pressure maps, and corresponding plurality of images of the human subject in lying poses from at least one imaging modality, including a red-green-blue (RGB) imaging modality, a long wavelength infrared (LWIR) imaging modality, or a depth imaging modality; and
training a model for generating the contact pressure map of a human lying on a surface with the dataset.

20. The method of claim 19, wherein the model can be expressed as:

$$L^{total} = \lambda_{pwrs} L_{2-1}^{pwrs} + \lambda_{phy} L_2^{phy};$$

wherein $$L_{2-1}^{pwrs} = \lambda_{L_2} \sum_{i=0}^{M} \sum_{j=0}^{N} (\hat{y}(i,j) - y(i,j))^2 (1/p(y(i,j) + \xi));$$

wherein $$L_2^{phy} = \left( c \sum_i \sum_j \hat{y}(i,j) - w_b \right)^2;$$

wherein $L_{2-1}^{pwrs}$ is a pixel-wise resampling (PWRS) loss;
wherein $L_2^{phy}$ is a physical loss;
wherein $\lambda_{pwrs}$ and $\lambda_{phy}$ stand for weights applied to each loss term, respectively;
wherein y(i, j) represents a pixel value at i and j coordinates of a pressure map;
wherein p(y(i, j)+ξ) is a density function of y and ξ is a hallucinated weight;
wherein M is a row size of the pressure map;
wherein N is a column size of the pressure map;
wherein $w_b$ stands for human body weight; and
wherein c is a contact area with a bed represented by each pixel of the pressure map.

* * * * *